(12) United States Patent
Gambhir et al.

(10) Patent No.: US 7,842,469 B2
(45) Date of Patent: Nov. 30, 2010

(54) BIOLUMINESCENCE RESONANCE ENERGY TRANSFER (BRET) SYSTEMS AND METHODS OF USE THEREOF

(75) Inventors: Sanjiv S. Gambhir, Portola Valley, CA (US); Abhijit De, Mountain View, CA (US)

(73) Assignee: Stanford University, Palo Alto, CA (US)

( * ) Notice: Subject to any disclaimer, the term of this patent is extended or adjusted under 35 U.S.C. 154(b) by 93 days.

(21) Appl. No.: 12/365,984

(22) Filed: Feb. 5, 2009

(65) Prior Publication Data

US 2010/0047813 A1 Feb. 25, 2010

Related U.S. Application Data

(62) Division of application No. 11/373,679, filed on Mar. 10, 2006, now Pat. No. 7,507,565.

(60) Provisional application No. 60/660,892, filed on Mar. 11, 2005.

(51) Int. Cl.
*G01N 33/53* (2006.01)

(52) U.S. Cl. ........................................... 435/7.1

(58) Field of Classification Search ........................ None
See application file for complete search history.

(56) References Cited

U.S. PATENT DOCUMENTS

| | | | |
|---|---|---|---|
| 2002/0177217 A1* | 11/2002 | Krieger et al. | 435/252.3 |
| 2003/0157519 A1 | 8/2003 | Zhang et al. | 435/6 |
| 2004/0214227 A1 | 10/2004 | Joly | 435/7.1 |

OTHER PUBLICATIONS

Loening et al. (Protein Engineering, Design & Selection 2006; 19(9): 391-400).*
Woo et al. (Protein Sci. 2008; 17:725-735).*
International Search Report and Written Opinion for PCT/US06/08632.
Xu, Yao., Piston, David W., and Johnson, Carl Hirschie, "A bioluminescence resonance energy transfer (BRET) systems: Application to Interacting Circadian Clock Proteins," *Proc. Natl. Acad. Sci. USA*, vol. 96, pp. 151-156, Jan. 1999.
Contag et al. (Journal of Magnetic Resonance Imaging. 2002; 16: 378-387).
Kappel et al. (1992) Current Opinion in biotechnology 3, 549, col. 2, para. 2).
Mullins et al. (1993) Hypertension 22, p. 631, col. 1, para. 1, lines 14-17).
Cameron (1997) Molec. Biol. 7, p. 256, col. 1-2, bridg. para.).
Sigmund (2000) Arteroscler. Throm. Vasc. Biol. 20, p. 1426, col. 1, para. 1, lines 1-7.
Niemann (1998) Transg. Res. 7, p. 73, col. 2, para. 2, line 12 to p. 73, col. 1, line 4.
Moreadith et al., J. Mol. Med., 1997, p. 214.
Pera et al. [Journal of Cell Science 113:5-10 (2000)].

* cited by examiner

*Primary Examiner*—Scott Long
(74) *Attorney, Agent, or Firm*—Thomas, Kayden, Horstemeyer & Risley, LLP

(57) ABSTRACT

Briefly described, embodiments of this disclosure include bioluminescence resonance energy transfer (BRET) systems, methods of detecting a protein-protein interaction, noninvasive methods for detecting the interaction of a first protein with a second protein within a living animal, methods to determine the efficacy of a test compound administered to modulate the interaction of a first protein with a second protein in a living animal, BRET vectors, kits relating to each of the above, transgenic cell or progeny thereof and/or animals relating to each of the above, and the like.

6 Claims, 17 Drawing Sheets

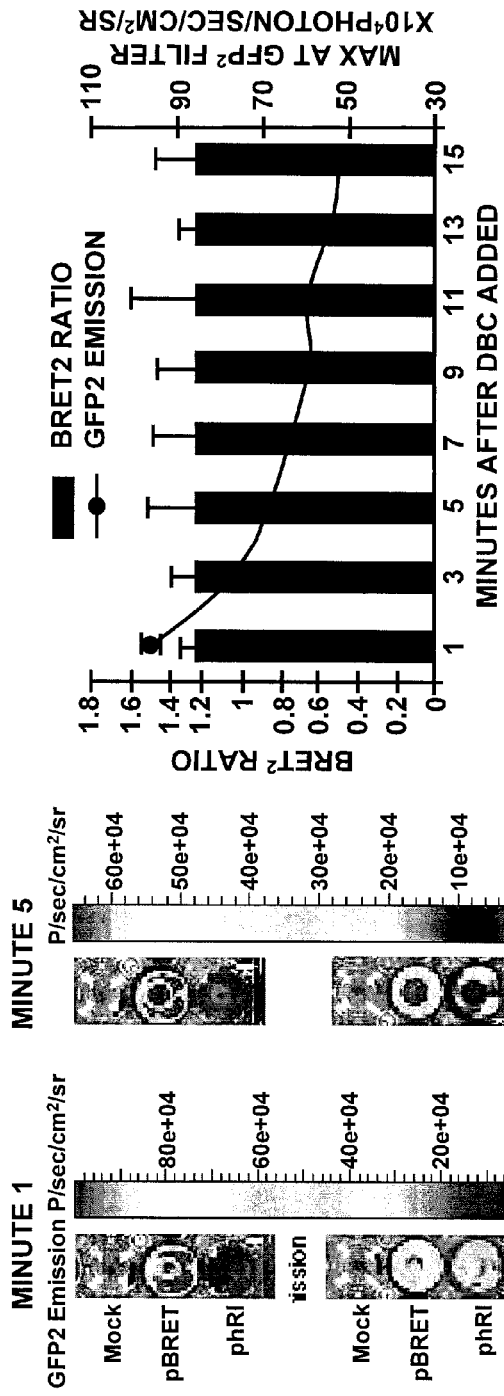
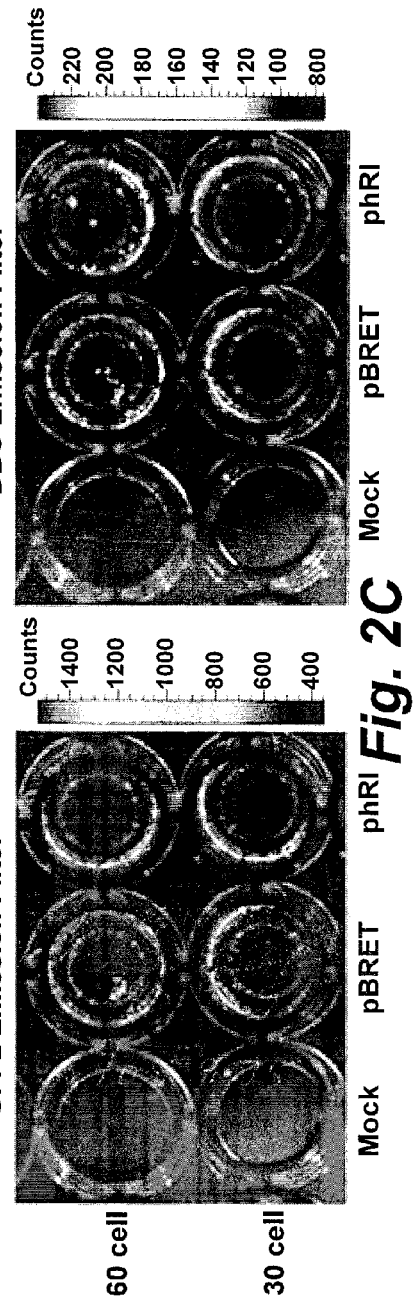
Fig. 2A
Fig. 2B
Fig. 2C

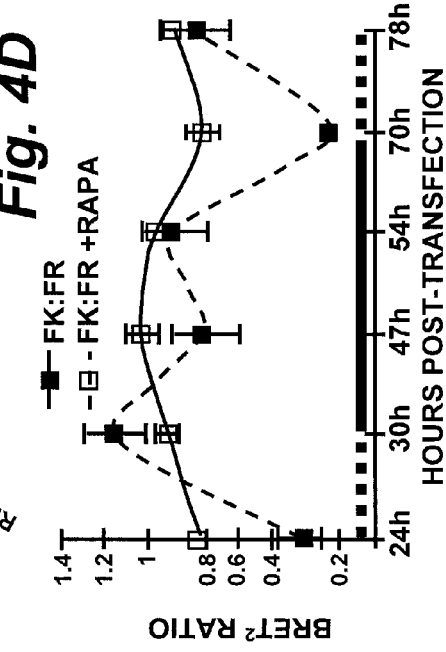
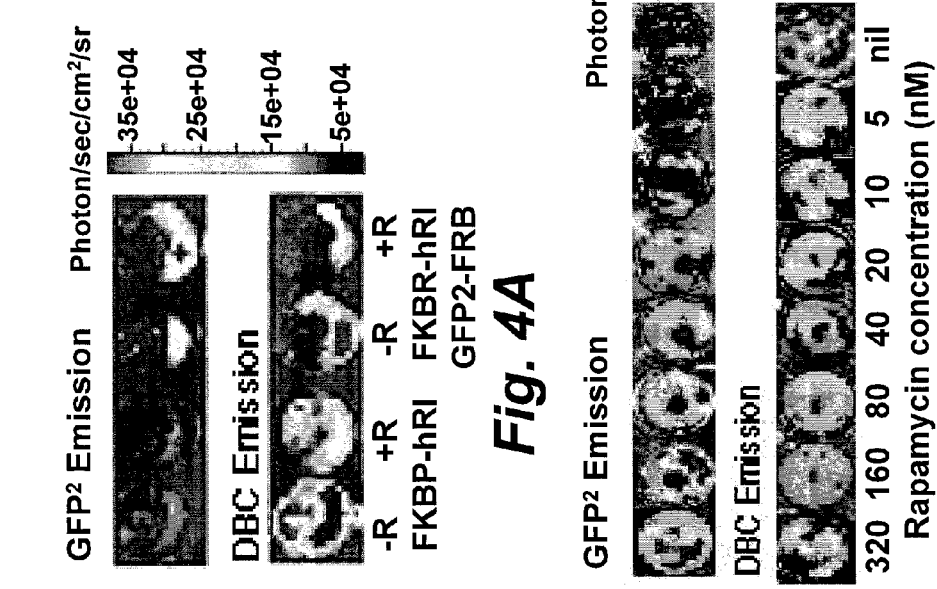
Fig. 4A
Fig. 4B
Fig. 4C
Fig. 4D

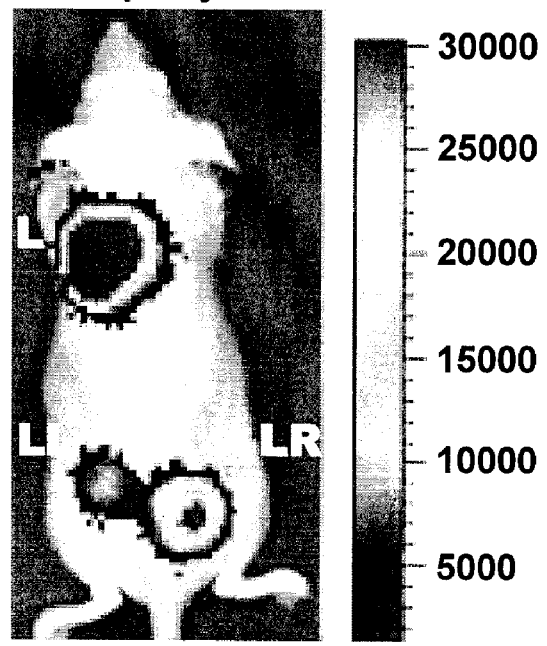
GFP2 emission
With Rapamycin   P/sec/cm2/sr
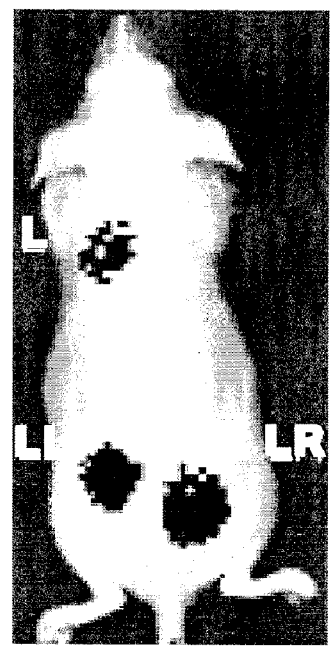
DBC emisision
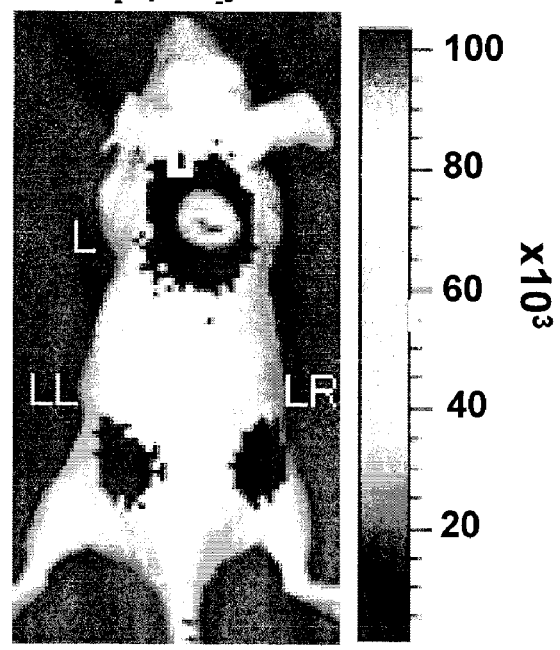
Without Rapamycin   P/sec/cm2/sr
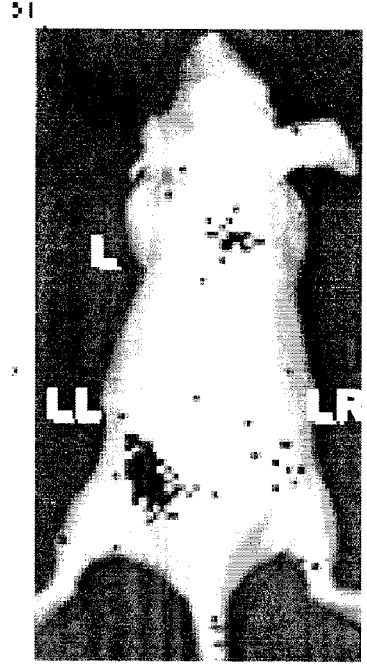
Fig. 6

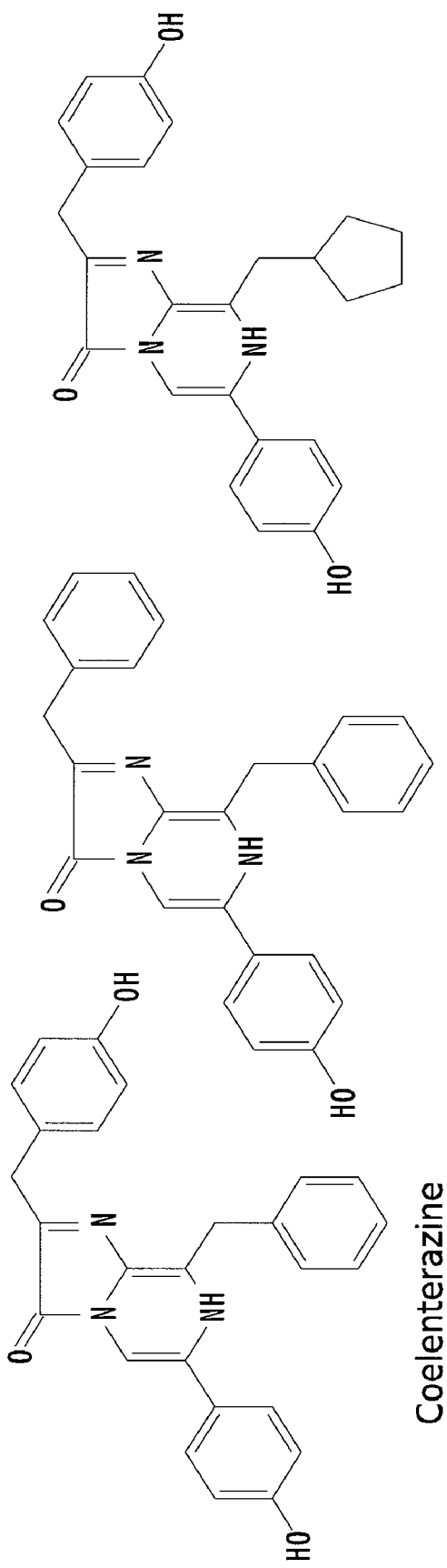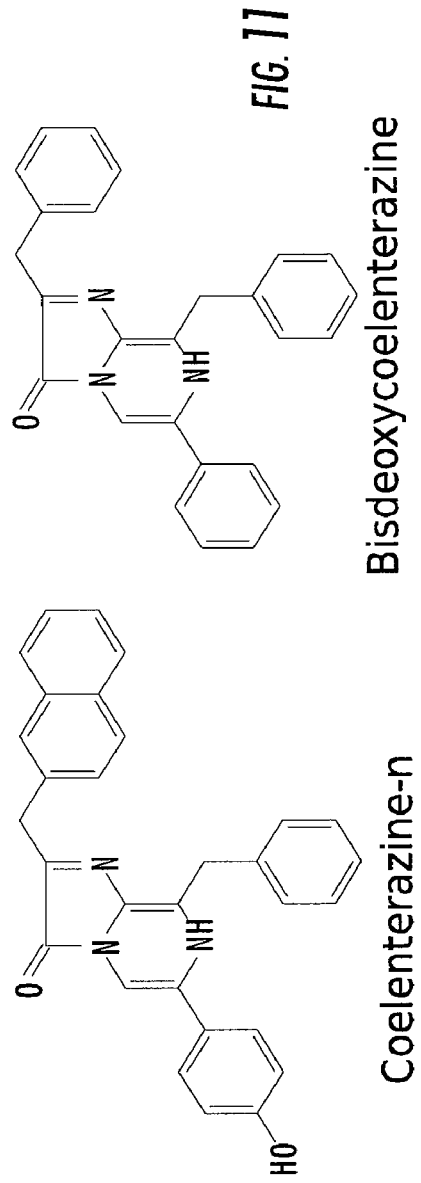
FIG. 11

```
R. reniformis      MISKVYDPEQRKRMITGPQWWARCKQMNVLDSFINYYDSEKHAENAVIFLHGNAASSYLWRHVVPHIEPVARQI
M. bovis           ------------MTAFGVEPYGQPKYLEIAGKRMAYIDEGK--GDAIVFQHGNPTSSYLWRNIMPHLEGLGRLV
M. tuberculosis    ------------MTAFGVEPYGQPKYLEIAGKRMAYIDEGK--GDAIVFQHGNPTSSYLWRNIMPHLEGLGRLV
M. smegmatis       --------------MPGSEPYGRLQYREINGKRMAYIDEAR--GDAIVFQHGNPSSSYLWRNVLPHTEGLGRLV
Sph. Paucimobilis  --------------SLGAKPFGEKKFIEIKGRRMAYIDEGT--GDPILFQHGNPTSSYLWRNIMPHCAGLGRLI
Br. japonicum      MS------------KPIEIEIRR--APVLGSSMAYRETGAQDAPVVLFLHGNPTSSHIWRNILPLVSPVAHCI
Mesorhi. loti      MSSKA-------NPPQPVATAPKRSQIPILDSTMSYVEAGAS-GPTVLFLHGNPTSSHIWRNIIPHVAPFGRCI
Mycobacterium GP1  MS------------EIGTGFPFDPHYVEVLGERMHYVDVGPRDGTPVLFLHGNPTSSYLWRNIIPHVAPSHRCI
Rho. rhodochrous   MS------------EIGTGFPFDPHYVEVLGERMHYVDVGPRDGTPVLFLHGNPTSSYLWRNIIPHVAPSHRCI
Agro. tumifaciens  --MKEHRHMTEKSPHSAFGDGAKAYDVPAFGLQIHTVEHGS--GAPIVFLHGNPTSSYLWRHIFRRLHGHGRLL R. reniformis      IPDLIGMGKSGK---SGNGSYRLLDHYKYLTAWFELLNLPKKIIFVGHDWGACLAFHYSYEHQDKIKAIVHAES
M. bovis           ACDLIGMGASDKLSPSGPDRYSYGEQRDFLFALWDALDLGDHVVLVLHDWGSALGFDWANQHRDRVQGIAFMEA
M. tuberculosis    ACDLIGMGASDKLSPSGPDRYSYGEQRDFLFALWDALDLGDHVVLVLHDWGSALGFDWANQHRDRVQGIAFMEA
M. smegmatis       ACDLIGMGASDKLDGSGPDSYHYHENRDYLFALWDALDLGDRVTLVLHDWGGALGFDWANRHRDRVAGIVHMET
Sph. Paucimobilis  ACDLIGMGDSDKLDPSGPERYTYAEHRDYLDALWEALDLGDRVVLVVHDWGSALGFDWARRHRERVQGIAYMEA
Br. japonicum      APDLIGFGQSGK----PDIAYRFFDHVRYLDAFIEQRGV-TSAYLVAQDWGTALAFHLAARRPDFVRGLAFMEF
Mesorhi. loti      APDLIGYGQSGK----PDIDYRFFDHVRYLDAFLDALDI-RDVLLVAQDWGTALAFHLAARRPQRVLGLAFMEF
Mycobacterium GP1  APDLIGMGKSDK----PDLDYFFDDHVRYLDAFIEALGL-EEVVLVIHDWGSALGFHWAKRNPERVKGIACMEF
Rho. rhodochrous   APDLIGMGKSDK----PDLDYFFDDHVRYLDAFIEALGL-EEVVLVIHDWGSALGFHWAKRNPERVKGIACMEF
Agro. tumifaciens  AVDLIGYGQSSK----PDIEYTLENQQRYVDAWFDALDL-RNVTLVLQDYGAAFGLNWASRNPDRVRAVAFFEP R. reniformis      VVDVIESWDEWPD----------IEEDIAL-IKSEE-GEKMVLENNFFVETMLPSKIMRKLEPEEFAAYLEPF
M. bovis           IVTPMT-WADWPP----------AVRGVFQGFRSPQ-GEPMALEHNIFVERVLPGAILRQLSDEEMNHYRRPF
M. tuberculosis    IVTPMT-WADWPP----------AVRGVFQGFRSPQ-GEPMALEHNIFVERVLPGAILRQLSDEEMNHYRRPF
M. smegmatis       VSVPME-WDDFPD----------EVAQMFRGLRSPQ-GEEMVLENNAFIEGVLPSIVMRTLSEEEMIHYRRPF
Sph. Paucimobilis  LAMPIE-WADFPE----------QDRDLFQAFRSQA-GEELVLQDNVFVEQVLPGLILRPLSEAEMAAYREPF
Br. japonicum      IR-PMPTWQDFHHTEVAEEQDHAEAARAVFRKFRTPGEGEAMILEANAFVERVLPGGIVRKLGDEEMAPYRTPF
Mesorhi. loti      IR-PFERWEDFHQ---------RPQAREMFKALRTPGVGEKLVLEDNVFVEKVLPASVLRAMSDDEMDVYRAPF
Mycobacterium GP1  IR-PIPTWDEWPE----------FARETFQAFRTADVGRELIIDQNAFIEGALPKFVVRPLTEVEMDHYREPF
Rho. rhodochrous   IR-PIPTWDEWPE----------FARETFQAFRTADVGRELIIDQNAFIEGALPKCVVRPLTEVEMDHYREPF
Agro. tumifaciens  VLRNIDSVDLSPE----------FVTRRAKLRQPGEGEIFVQQENRFLTELFPWFFLTPLAPEDLRQYQTPF R. reniformis      KEKGEVRRPTLSWPREIPLVKGGKPDVVQIVRNYNAYLRASDDLPKMFIESDPGFFSNA--IVEGAKKFPENTF
M. bovis           VNGGEDRRPTLSWPRNLPID-GEPAEVVALVNEYRSWLEETD-MPKLFINAEPGAIITG-RIRDYVRSWPNQTE
M. tuberculosis    VNGGEDRRPTLSWPRNLPID-GEPAEVVALVNEYRSWLEETD-MPKLFINAEPGAIITG-RIRDYVRSWPNQTE
M. smegmatis       LNAGEDRRPTLSWPRDVPLA-GEPAEVVAVIEDFGEWLATSD-IPKLFIRADPGVIQGKQRILDIVRSWPNQTE
Sph. Paucimobilis  LAAGEARRPTLSWPRQIPIA-GTPADVVAIARDYAGWLSESP-IPKLFINAEPGSLTTG-RMRDFCRTWPNQTE
Br. japonicum      PTP-ESRRPVLAFPRELPIA-GEPADVYEALQSAHAALAASS-YPKLLFTGEPGALVSPEFAERFAASLTRCAL
Mesorhi. loti      PTP-QSRKPVLRLPREMPIE-GQPADVAAISAHDHRALRLST-YPKLLFAGDPGALIGPQAAREFAAGLKNCSF
Mycobacterium GP1  LKP-VDREPLWRFPNELPIA-GEPANIVALVEAYMNWLHQSP-VPKLLFWGTPGVLISPAEAARLAESLPNCKT
Rho. rhodochrous   LKP-VDREPLWRFPNELPIA-GEPANIVALVEAYMNWLHQSP-VPKLLFWGTPGVLIPPAEAARLAESLPNCKT
Agro. tumifaciens  PTP-HSRKAILAGPRNLPVD-GEPASTVAFLEQAVNWLNTSD-TPKLLLTFKPGFLLTDAILKWSQVTIRNLEI R. reniformis      VKV-KGLHFSQEDAPDEMGKYIKSFVERVLKNEQ---------
M. bovis           ITV-PGVHFVQEDSPEEIGAAIAQFVRQLRSAAGV--------
M. tuberculosis    ITV-PGVHFVQEDSPEEIGAAIAQFVRRLRSAAGV--------
M. smegmatis       ITV-PGTHFLQEDSAD---------------------------
Sph. Paucimobilis  ITV-AGAHFIQEDSPDEIGAAIAAFVRRLRPA-----------
Br. japonicum      IRLGAGLHYLQEDHADAIGRSVAGWIAGIEAVRP--QLAA---
Mesorhi. loti      INLGPGAHYLQEDHADAIGRAIASWLPEVVLANQTDELA----
Mycobacterium GP1  VDIGPGLHFLQEDNPDLIGSEIARWLPALIVGKSIEFDGGWAT
Rho. rhodochrous   VDIGPGLHYLQEDNPDLIGSEIARWLPAL--------------
Agro. tumifaciens  EAAGAGIHFVQEEQPETIARLLDAWLTRIAGN-----------
```

FIG. 13A

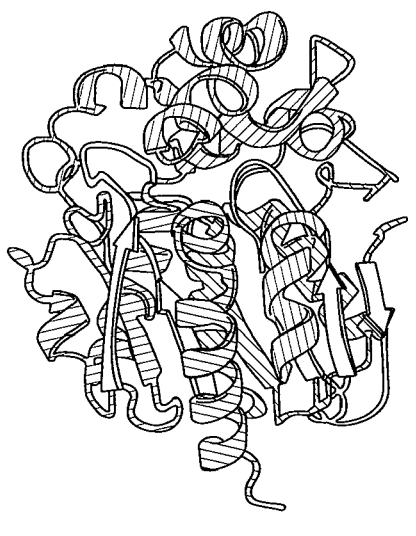 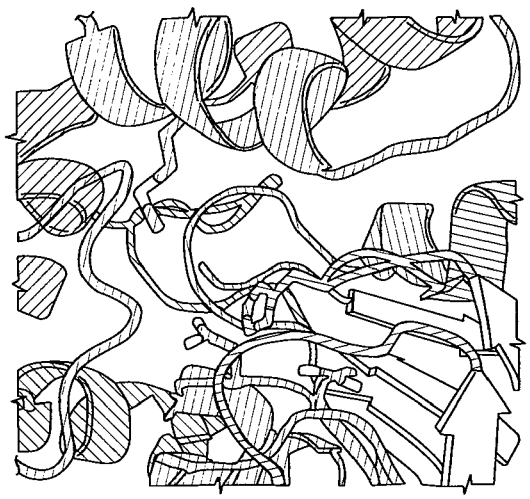
FIG. 13B                    FIG. 13C

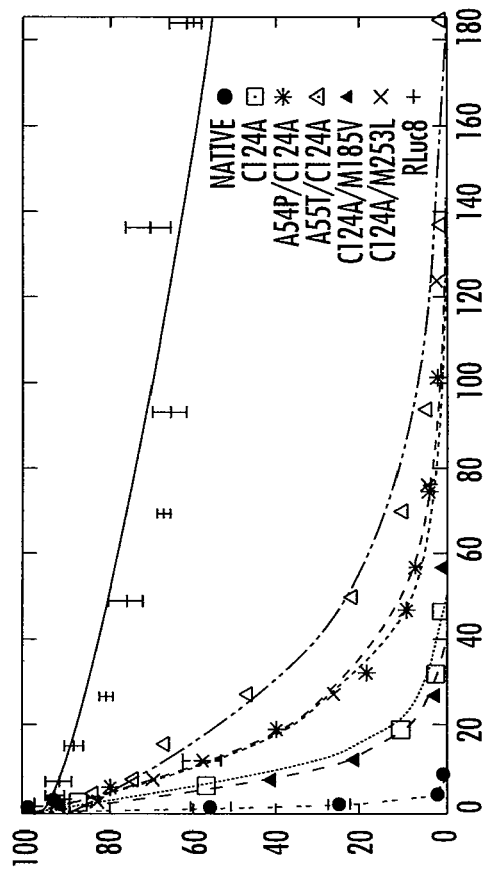
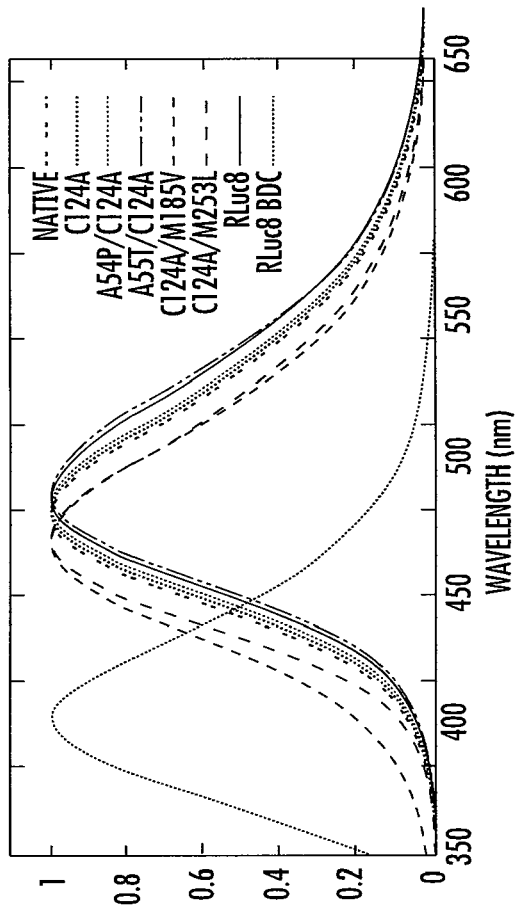
FIG. 14A
FIG. 14B

SEQUENCE LISTING

<160> NUMBER OF SEQ ID NOS: 3

<210> SEQ ID NO 1
<211> LENGTH: 311
<212> TYPE: PRT
<213> ORGANISM: Artificial Sequence
<220> FEATURE:
<223> OTHER INFORMATION: Chemically synthesized Renilla Luciferase

<400> SEQUENCE: 1

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

<210> SEQ ID NO 2
<211> LENGTH: 311
<212> TYPE: PRT
<213> ORGANISM: Artificial Sequence

```
<220> FEATURE:
<223> OTHER INFORMATION: Chemically synthesized Renilla Luciferase

<400> SEQUENCE: 2

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 3
<211> LENGTH: 311
<212> TYPE: PRT
<213> ORGANISM: Artificial Sequence
<220> FEATURE:
<223> OTHER INFORMATION: Chemically Synthesized Renilla Luciferase

<400> SEQUENCE: 3

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
```

-continued

```
            20                  25                  30
Phe Ile Asn Tyr Tyr Asp Ser Glu Lys His Ala Glu Asn Ala Val Ile
         35                  40                  45
Phe Leu His Gly Asn Ala Thr Ser Ser Tyr Leu Trp Arg His Val Val
50                   55                  60
Pro His Ile Glu Pro Val Ala Arg Cys Ile Ile Pro Asp Leu Ile Gly
65                   70                  75                  80
Met Gly Lys Ser Gly Lys Ser Gly Asn Gly Ser Tyr Arg Leu Leu Asp
             85                  90                  95
His Tyr Lys Tyr Leu Thr Ala Trp Phe Glu Leu Leu Asn Leu Pro Lys
            100                 105                 110
Lys Ile Ile Phe Val Gly His Asp Trp Gly Ala Ala Leu Ala Phe His
            115                 120                 125
Tyr Ala Tyr Glu His Gln Asp Arg Ile Lys Ala Ile Val His Met Glu
    130                 135                 140
Ser Val Val Asp Val Ile Glu Ser Trp Asp Glu Trp Pro Asp Ile Glu
145                 150                 155                 160
Glu Asp Ile Ala Leu Ile Lys Ser Glu Glu Gly Glu Lys Met Val Leu
                165                 170                 175
Glu Asn Asn Phe Phe Val Glu Thr Val Leu Pro Ser Lys Ile Met Arg
                180                 185                 190
Lys Leu Glu Pro Glu Glu Phe Ala Ala Tyr Leu Glu Pro Phe Lys Glu
            195                 200                 205
Lys Gly Glu Val Arg Arg Pro Thr Leu Ser Trp Pro Arg Glu Ile Pro
210                 215                 220
Leu Val Lys Gly Gly Lys Pro Asp Val Val Gln Ile Val Arg Asn Tyr
225                 230                 235                 240
Asn Ala Tyr Leu Arg Ala Ser Asp Asp Leu Pro Lys Leu Phe Ile Glu
                245                 250                 255
Ser Asp Pro Gly Phe Phe Ser Asn Ala Ile Val Glu Gly Ala Lys Lys
            260                 265                 270
Phe Pro Asn Thr Glu Phe Val Lys Val Lys Gly Leu His Phe Leu Gln
            275                 280                 285
Glu Asp Ala Pro Asp Glu Met Gly Lys Tyr Ile Lys Ser Phe Val Glu
    290                 295                 300
Arg Val Leu Lys Asn Glu Gln
305                 310
```

BIOLUMINESCENCE RESONANCE ENERGY TRANSFER (BRET) SYSTEMS AND METHODS OF USE THEREOF

CROSS-REFERENCE TO RELATED APPLICATION

This application is a divisional application of copending U.S. utility Application entitled "Bioluminescence Resonance Energy Transfer (BRET) Systems and Methods of Use Thereof", having Ser. No. 11/373,679, filed Mar. 10, 2006, which claims priority to U.S. provisional applications entitled, "Bioluminescence Resonance Energy Transfer (BRET) Systems And Methods Of Use Thereof," having Ser. No. 60/660,892, filed on Mar. 11, 2005; and "Improved Luciferases And Methods For Making And Using The Same," having Ser. No. 60/714,969, filed on Sep. 7, 2005, which are both entirely incorporated herein by reference.

STATEMENT REGARDING FEDERALLY SPONSORED RESEARCH OR DEVELOPMENT

This invention was made with government support awarded by the NIH Grant NCI ICMIC P50 CA114747. The government has certain rights in the invention(s).

BACKGROUND

Luminescence is a phenomenon in which energy is specifically channeled to a molecule to produce an excited state. Return to a lower energy state is accompanied by release of a photon. Luminescence includes fluorescence, phosphorescence, chemiluminescence and bioluminescence. Bioluminescence is the process by which living organisms emit light that is visible to other organisms. Where the luminescence is bioluminescence, creation of the excited state derives from an enzyme catalyzed reaction. Luminescence can be used in the analysis of biological interactions.

Interactions between proteins and other molecules play a key regulatory role in almost every biological process. For example, cytosolic and cell surface protein-protein interactions play major roles in normal cellular functions and biological responses. In particular, many cytosolic and cell surface protein-protein interactions are involved in disease pathways. For example, attacks by pathogens such as viruses and bacteria on mammalian cells typically begin with interactions between viral or bacterial proteins and mammalian cell surface proteins. In addition, many protein-protein interactions between factors in cellular transcriptional machineries are also valuable drug targets. Protein-protein interactions are also involved, for example, in the assembly of enzyme subunits; in antigen-antibody reactions; in forming the supramolecular structures of ribosomes, filaments, and viruses; in transport; and in the interaction of receptors on a cell with growth factors and hormones. Products of oncogenes can give rise to neoplastic transformation through protein-protein interactions. Thus, many techniques have been developed to identify and characterize these interactions.

One technique for assessing protein-protein interaction is based on fluorescence resonance energy transfer (FRET). In this process, one fluorophore (the "donor") transfers its excited-state energy to another fluorophore (the "acceptor"), which usually emits fluorescence of a different color. According to Forster equation (Forster, T., (1948) Ann. Physik., 2, 55 and Forster, T., (1960) Rad. Res. Suppl., 2, 326), FRET efficiency depends on five parameters: (i) the overlap between the absorption spectrum of the second fluorophore and the emission spectrum of the first fluorophore, (ii) the relative orientation between the emission dipole of the donor and the absorption dipole of the acceptor, (iii) the distance between the fluorophores, (iv) the quantum yield of the donor, and (v) the extinction coefficient of the acceptor.

FRET has been used to assay protein-protein proximity in vitro and in vivo by chemically attaching fluorophores such as fluorescein and rhodamine to pairs of purified proteins and measuring fluorescence spectra of protein mixtures or cells that were microinjected with the labeled proteins (Adams et al, (1991) Nature, 349, 694-697).

The cloning and expression of Green Fluorescent Protein (GFP) in heterologous systems opened the possibility of genetic attachment of fluorophores to proteins. In addition, the availability of GFP mutants with altered wavelengths (Heim et al., (1994) Proc. Natl. Acad. Sci. USA., 91, 12501-12504) allowed their use as FRET pairs.

An attractive application allowed by GFP-based FRET is the in vivo assay of protein interactions in organisms other than yeast. For example, fusion of GFP and BFP to the mammalian transcriptional factor Pit-1 showed homo-dimerization of Pit-1 in live HeLa cells (Periasamy, A. and Day, R. N., (1998) J. Biomed. Opt., 3, 1-7). In this type of assay, interactions can be examined in the proteins' native organism, such that cell-type specific modifications and/or compartmentalization of the proteins are preserved. Additionally, compartmentalization of these interacting proteins is potentially visible in the microscope.

FRET, however, has several limitations. As with any fluorescence technique, photobleaching of the fluorophore and autofluorescence of the cells/tissue can significantly restrict the usefulness of FRET, and, in highly autofluorescent tissues, FRET is essentially unusable. Also, if the excitation light easily damages the tissue, the technique may be unable to give a value for healthy cells. Finally, if the cells/tissues to be tested are photoresponsive (e.g., retina), FRET may be impractical because as soon as a measurement is taken, the photoresponse may be triggered.

SUMMARY

Briefly described, embodiments of this disclosure include bioluminescence resonance energy transfer (BRET) systems, methods of detecting a protein-protein interaction, noninvasive methods for detecting the interaction of a first protein with a second protein within a living animal, methods to determine efficacy of a test compound administered to modulate the interaction of a first protein with a second protein in a living animal, BRET vectors, kits relating to each of the above, transgenic cells or progeny thereof and/or animals relating to each of the above, and the like.

An embodiment of a BRET system, among others, includes: a first fusion protein including a first target protein and a bioluminescence donor molecule, wherein the bioluminescence donor molecule is a mutated *Renilla* Luciferase protein selected from: SEQ ID NO: 2 or conservatively modified variants thereof; a second fusion protein including a second target protein and a fluorescent acceptor molecule; and a bioluminescence initiating compound.

An embodiment of a BRET system, among others, includes: a first fusion protein including a first target protein and a bioluminescence donor molecule, wherein the bioluminescence donor molecule is selected from a *Renilla* Luciferase protein and a mutated *Renilla* Luciferase protein; a second fusion protein including a second target protein and a fluorescent acceptor molecule; and a bioluminescence initiating compound, wherein when the first fusion protein and the second fusion protein are within about 50 to 100 Angstroms of one another and in the presence of the bioluminescence initiating compound, the bioluminescence donor molecule is adapted to interact with the bioluminescence initiating compound, wherein the bioluminescence donor molecule is adapted to emit a bioluminescence energy upon interaction with the bioluminescence initiating compound, wherein the fluorescent acceptor molecule is adapted to accept the bioluminescence energy, and wherein fluorescent acceptor molecule is adapted to emit a fluoresence energy after accepting the bioluminescence energy.

An embodiment of a method of detecting a protein-protein interaction, among others, includes: providing a first vector that includes a first polynucleotide that encodes a first fusion protein, wherein the first fusion protein includes a first target protein and a bioluminescence donor molecule, wherein the bioluminescence donor molecule is selected from a *Renilla* Luciferase protein and a mutated *Renilla* Luciferase protein; expressing the first polynucleotide to produce the first fusion protein in a system; providing a second vector that includes a second polynucleotide sequence that encodes a second fusion protein including a second target protein and a fluorescent acceptor molecule; expressing the second polynucleotide to produce the second fusion protein in a system; providing a bioluminescence initiating compound, wherein a bioluminescence energy is emitted from the bioluminescence donor molecule upon interaction with the bioluminescence initiating compound when the first fusion protein and the second fusion protein are within about 50 to 100 Angstroms of each other, and wherein a fluoresence energy is emitted from the fluorescent acceptor molecule upon accepting the bioluminescence energy; and detecting an energy from one of the bioluminescence energy and the fluoresence energy.

An embodiment of noninvasive methods for detecting the interaction of a first protein with a second protein within a living animal, among others, includes: providing a first vector, comprising a first polynucleotide that encodes a first fusion protein, wherein the first fusion protein includes a first target protein and a bioluminescence donor molecule, wherein the bioluminescence donor molecule is selected from a *Renilla* Luciferase protein and a mutated *Renilla* Luciferase protein; providing a second vector, comprising a polynucleotide that encodes a second fusion protein including a second target protein and a fluorescent acceptor molecule; administering the first vector and the second vector to the living animal; generating the first fusion protein in the living animal; generating the second fusion protein in the living animal; administering a bioluminescence initiating compound to the living animal, wherein a bioluminescence energy is emitted from the bioluminescence donor molecule upon interaction with the bioluminescence initiating compound when the first fusion protein and the second fusion protein are within about 50 to 100 Angstroms of each other, wherein a fluoresence energy is emitted from the fluorescent acceptor molecule upon accepting the bioluminescence energy; and detecting an energy from one of the bioluminescence energy and the fluoresence energy in the living animal.

An embodiment of a method to determine efficacy of a test compound administered to modulate the interaction of a first protein with a second protein in a living animal, includes: providing a first vector, comprising a first polynucleotide that encodes a first fusion protein, wherein the first fusion protein includes a first target protein and a bioluminescence donor molecule, wherein the bioluminescence donor molecule is selected from a *Renilla* Luciferase protein and a mutated *Renilla* Luciferase protein; providing a second vector, comprising a second polynucleotide that encodes a second fusion protein including a second target protein and a fluorescent acceptor molecule; administering the first vector and the second vector to the living animal; generating the first fusion protein in the animal; generating the second fusion protein in the animal; administering the test compound to the living animal; administering a bioluminescence initiating compound to the living animal, wherein a bioluminescence energy is emitted from the bioluminescence donor molecule upon interaction with the bioluminescence initiating compound when the first fusion protein and the second fusion protein are within about 50 to 100 Angstroms of each other, wherein a fluoresence energy is emitted from the fluorescent acceptor molecule upon accepting the bioluminescence energy; and detecting an energy from one of the bioluminescence energy and the fluoresence energy in the living animal.

An embodiment of BRET vectors, among others, includes: a polynucleotide sequence encoding a first target protein, and a bioluminescence donor molecule, wherein the bioluminescence donor molecule comprises a mutated *Renilla* Luciferase protein having SEQ ID NO: 3 or conservatively modified variants thereof.

An embodiment of kits, among others, includes: a polynucleotide encoding a bioluminescence donor molecule, wherein the bioluminescence donor molecule comprises a mutated *Renilla* Luciferase protein having SEQ ID NO: 3 or conservatively modified variants thereof; and directions for use.

An embodiment of transgenic cells or progeny thereof, among others, includes: a transgene comprising a polynucleotide encoding a bioluminescence donor molecule, wherein the bioluminescence donor molecule comprises a mutated *Renilla* Luciferase protein having SEQ ID NO: 3 or conservatively modified variants thereof.

An embodiment of transgenic cells or progeny thereof, among others, includes: a polynucleotide encoding a bioluminescence donor molecule, wherein the bioluminescence donor molecule comprises a mutated *Renilla* Luciferase protein having SEQ ID NO: 3 or conservatively modified variants thereof.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 2 illustrates a simultaneous visualization and quantitation of BRET signals from various quantities of total cellular proteins in well plates using a cooled CCD camera. BRET assays were first performed with serially diluted total proteins isolated from 293T cells at 24 hours after being transiently transfected with pBRET2 and phRluc plasmids along with 1/10th amount of CMV-Fluc plasmid as transfection control (FIG. 2A). CCD images shown in FIG. 2C represent the image as captured using GFP2 or DBC filter from well plate containing exact quantities of cellular lysates from pBRET$^2$ transfected cells. The line on the chart in FIG. 2B represents average radiance of GFP emission, where the bars represent the calculated BRET ratio at each respective concentration of protein. Error bars represent SEM.

FIG. 3A illustrates CCD images of 293T cells in 24 well plate with added Coelenterazine400a (DBC) on three consecutive wells transfected as marked. The image was captured at each alternate minute with one-minute integration time using either GFP$^2$ or DBC filters.

FIG. 3B illustrates a chart, where the line on the chart represents average radiance as obtained by drawing ROI over each well as in A at each time points measured from pBRET$^2$ transfected well using GFP$^2$ filter. BRET$^2$ ratios were also calculated at each time points as represented by the bars. Error bars represent SEM.

FIG. 3C illustrates CCD camera images of live cells in 96 well plate using a zoom lens. 293T cells transiently transfected (with 65% transfection efficiency) with plasmids as marked were imaged 24 hours after transfection. The images were captured successively using either GFP$^2$ or DBC filters with 2 minute integration time on each filter after adding Coelenterazine400a (DBC) (0.3 μg/well in 96 well format). The number of cells as marked represents the exact number of cells plated in the corresponding wells 4 hours prior scanning. The image scale is background-subtracted and cosmic-corrected.

FIGS. 4A through 4D illustrate BRET signals from rapamycin mediated FKBP12 and FRB interaction in live cells. FIG. 4A illustrates CCD camera images of 293T cells either transfected with pFKBP12-hRluc alone or co-transfected with pFKBP12-hRluc and pGFP$^2$-FRB along with CMV-Fluc control plasmid, added with or without rapamycin as indicated (+R or −R), showing that specific GFP$^2$ signal can be obtained only when the two proteins interact forming heterodimers in the presence of rapamycin. Note that on rapamycin added wells, DBC photon emission yield is lower than otherwise.

FIG. 4B illustrates a chart showing significant BRET$^2$ ratio (bar) and GFP$^2$ emission light (line) as can be obtained only by specific interactions of FKBP12 and FRB in presence of rapamycin. 293T cells transfected with phRluc alone (RL), pFKBP12-hRluc and pGFP$^2$-FRB co-transfected (F-RL: GFP-F), phRluc and pGFP$^2$ co-transfected (RL: GFP), and mock in presence (+R) or absence (−R) of rapamycin were shown. Error bars for GFP$^2$ emission signal represents standard error of mean.

FIG. 4C illustrates CCD images of the well plate using different filters showing BRET$^2$ signal change with varying rapamycin dose. The experiment was done by co-transfecting 293T cells with pFKBP12-hRluc and pGFP$^2$-FRB in 24 well plate. After transfection the wells were incubated overnight with culture media containing a specified (nM) dose of rapamycin. Twenty-four hours later, Coelenterazine400a (DBC) was added (1 μg/well) after removing the media, and the plate was imaged at GFP$^2$ filter first and DBC filter for the following minute.

FIG. 4D illustrates a chart showing the dynamic nature of a BRET signal. 293T cells transfected with pFKBP12-hRluc and pGFP$^2$-FRB plasmids in a 1:1 ratio were distributed in equal numbers in a 24 well plate. The dashed line represents the BRET$^2$ ratio over time, where transfected cells were maintained throughout with rapamycin (160 nM). The solid line represents the BRET$^2$ ratio over time, where rapamycin was added and withdrawn at different time points from the incubating media of the transfected cells. As shown by the cross-hatched zone on the X-axis marked as +R or −R, rapamycin was added to the experimental cells after first scanning at 24 hours. After 6 hours incubation another scan was performed (30 hours). Then the rapamycin was withdrawn and the cells were scanned successively at 47, 54 and 70 hours, by which BRET$^2$ signal reduced significantly in comparison to the control cells, which were maintained in rapamycin containing media at all time. Finally, rapamycin was added again in the experimental wells at 70 hours and scanned after 8 hours of incubation (78 hours) to show that bringing the rapamycin back in solution can still affect increase in the BRET$^2$ signal.

FIG. 5A illustrates a dorsal view of a nude mouse subcutaneously implanted with $3 \times 10^6$ 293T cells transiently transfected with either phRluc (L) or pBRET$^2$ (R) on the lower flank. An hour later, 20 μg Coelenterazine400a (DBC) was injected intravenously (i.v.) and scanned successively with 5 minutes integration time using GFP$^2$ and DBC filter.

FIG. 5B illustrates a ventral view of a nude mouse intravenously injected (i.v.) with $3 \times 10^6$ 293T cells transiently transfected with pBRET$^2$. After 30 minutes of cell injection, 100 μg Coelenterazine400a (DBC) was injected and scanned successively for 5 minutes integration time using GFP$^2$, DBC and open filter position for total light. Note that blue shifted (400 nm peak) DBC-RLUC emission signal could not get through from the lung; however, an open filter image confirms the locations of cells. Note that RL denotes right lung, while LL denotes left lung.

FIG. 5C illustrates a graph that described the organs after they were scanned. The thoracic organs from the chest area were dissected, total protein isolated from each, and the *Renilla* Luciferase assay was performed in triplicates using a dual luciferase assay kit. The chart represents the RLU/μg protein obtained from thoracic tissue samples of the mouse, which correlates with the higher signal on RL in comparison to the LL as visualized on the CCD image as on B.

FIG. 6 illustrates the detection of in vivo BRET$^2$ signal from specific protein-protein interaction in nude mice. The dorsal view of a nude mouse implanted with $5 \times 10^6$ 293T cells either transiently transfected with pBRET$^2$ (L) or with pFKBP12-hRluc (LL) alone or co-transfected with pFKBP12-hRluc and pGFP²-FRB (LR) in the presence (upper panel) or absence (lower panel) of rapamycin. Mice that received the small molecule mediator drug, rapamycin (5 mg/kg) were injected (i.p.) immediately after cell implantation. The scan was performed 7 hours after drug administration. Mice were scanned for 5 minutes integration time using either GFP² or DBC filters in succession by injecting with 25 μg Coelenterazine400a (DBC) intravenously.

FIGS. 8A through 8D illustrate that even though the two established cell lines produce an equivalent amount of the fusion protein, fixed numbers of the GFP2-Rluc8 cells produce much higher photon than GFP2-Rluc cells. Cells were plated 4 hours prior to the CCD camera imaging. ROI values from corresponding wells were plotted (bars) as obtained from image data using either donor or acceptor filter. The line represents the calculated BRET ratios at each time point of measurements. Error bars represent SEM.

FIG. 10A illustrates a CCD camera image of a representative mouse implanted with 500,000 GFP2-Rluc cells on the left shoulder (L) and the same number of GFP2-Rluc8 cells on the right flank (R) at subcutaneous tissue depth. The mice were imaged by injecting 25 ug Coelenterazine400a (DBC) intravenously using a 2 minutes image acquisition time. Images were captured in sequence using an acceptor filter first followed by a donor filter, after a single dose of Coelenterazine400a.

FIG. 10B illustrates a CCD camera image of a representative mouse implanted with 2 million GFP2-Rluc8 cells by intravenous injection. These mice were imaged by injecting 75 ug Coelenterazine 400a intravenously using a 3 minutes image acquisition time. Images were captured in sequence using an acceptor filter first followed by a donor filter, after a single dose of Coelenterazine400a.

FIG. 11 illustrates the chemical structures of coelenterazine and several analogs.

FIG. 13A illustrates the homology model of *Renilla* luciferase based on its similarity to the haloalkane dehalogenase LinB. The region of the enzyme from residue 35 to 309 was successfully modeled using Swiss-Model and is shown in FIG. 13B. The N-terminus is blue and the C-terminus is red. The presumptive active site is located at the intersection of the red, green, and green-cyan loops.

FIG. 13C illustrates a close up of the homology model showing the potential active site. The side chains for the potential active site residues D120, E144, and H285 are shown, along with the mutation site M185.

FIG. 14A illustrates mouse serum stability data for RLuc, RLuc8, and several other mutations. Protein was incubated in mouse serum at 37° C. in triplicate, with aliquots removed at various times to determine the remaining luciferase activity. The error bars represent the standard error of the mean, and the lines drawn between the points are from mono-exponential curve fits.

FIG. 14B illustrates a normalized bioluminescence emission spectra for RLuc, RLuc8, and several other mutations. Most mutations resulted in only small shifts from the emission spectra of the native luciferase enzyme. The normalized emission spectrum of RLuc8 when used with bisdeoxycoelenterazine or Coelenterazine400a (bdc) is also included for comparison.

DETAILED DESCRIPTION

Figure 1A:
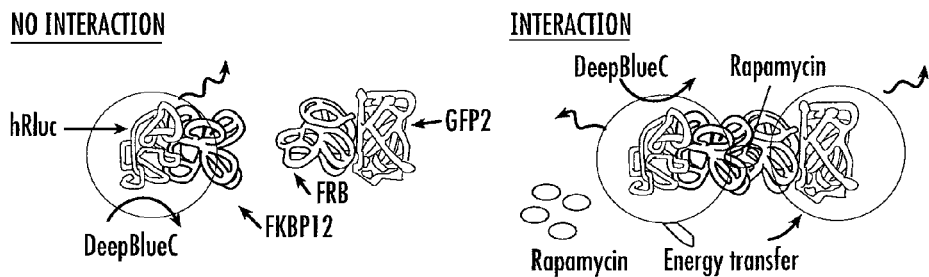
FIG. 1A illustrates a schematic showing small molecule mediated protein-protein interactions leading to bioluminescence resonance energy transfer (BRET). FKBP12 is fused to the N-terminus of a RLUC donor protein (hRluc), and a FRAP binding domain (FRB) is fused to the C-terminus of a GFP$^2$ acceptor protein. When the genes encoding for both of these two fusion proteins are expressed inside cells, and rapamycin is present to mediate FRB-FKBP12 interaction, then resonance energy transfer occurs. This BRET signal can be detected by using the Deep Blue Coelenterazine (DBC) substrate for RLUC.

Embodiments of the present disclosure will employ, unless otherwise indicated, techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

Bioluminescence (BL) is defined as emission of light by living organisms that is well visible in the dark and affects visual behavior of animals (See e.g., Harvey, E. N. (1952). *Bioluminescence*. New York: Academic Press; Hastings, J. W. (1995). Bioluminescence. In: *Cell Physiology* (ed. by N. Speralakis). pp. 651-681. New York: Academic Press.; Wilson, T. and Hastings, J. W. (1998). Bioluminescence. *Annu Rev Cell Dev Biol* 14, 197-230.). Bioluminescence does not include so-called ultra-weak light emission, which can be detected in virtually all living structures using sensitive luminometric equipment (Murphy, M. E. and Sies, H. (1990), *Meth. Enzymol.* 186, 595-610; Radotic, K, Radenovic, C, Jeremic, M. (1998), *Gen Physiol Biophys* 17, 289-308). Bioluminescence also does not include weak light emissions, which most probably does not play any ecological role, such as the glowing of bamboo growth cone (Totsune, H., Nakano, M., Inaba, H. (1993), *Biochem. Biophys. Res Comm.* 194, 1025-1029). Bioluminescence also does not include emission of light during fertilization of animal eggs (Klebanoff, S. J., Froeder, C. A., Eddy, E. M., Shapiro, B. M. (1979), *J. Exp. Med.* 149, 938-953; Schomer, B. and Epel, D. (1998), *Dev Biol* 203, 1-11).

"Bioluminescent donor protein" refers to a protein capable of acting on a bioluminescent initiator molecule substrate to generate bioluminescence.

"Fluorescent acceptor molecule" refers to any molecule that can accept energy emitted as a result of the activity of a bioluminescent donor protein, and re-emit it as light energy.

"Bioluminescent initiator molecule" is a molecule that can react with a bioluminescent donor protein to generate bioluminescence.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide includes conservatively modified variants. A substituted or inserted amino acid residue may or may not be one encoded by the genetic code. A variant of a polypeptide may be naturally occurring, such as an allelic variant, or it may be a variant that is not known to occur naturally.

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (O); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptides as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. (Robertson, et al., *J. Am. Chem. Soc.,* 113: 2722, 1991; Ellman, et al., *Methods Enzymol.,* 202: 301, 1991; Chung, et al., *Science,* 259: 806-9, 1993; and Chung, et al., *Proc. Natl. Acad. Sci. USA,* 90: 10145-9, 1993). In a second method, translation is carried out in Xenopus oocytes by microinjection of mutated mRNA and chemically aminoacylated suppressor tRNAs (Turcatti, et al., *J. Biol. Chem.,* 271: 19991-8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., *Biochem.,* 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., *Protein Sci.,* 2: 395-403, 1993).

As used herein, the term "polynucleotide" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompasses a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alias.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain. Codons correspond to specific amino acids (as defined by the transfer RNAs) or to start and stop of translation by the ribosome.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

A cell has been "transformed" or "transfected" by a nucleic acid sequence such as an exogenous or a heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations. The nucleic acid may be in the form of naked DNA or RNA, associated with various proteins or the nucleic acid may be incorporated into a vector.

A "heterologous" region of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "vector" or "expression vector" is used to denote a DNA molecule, linear or circular, which includes a segment encoding a polypeptide of interest operably linked to additional segments that provide for its transcription and translation upon introduction into a host cell or host cell organelles. Such additional segments include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of one or more of the above.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

As used herein, the term "hybridization" refers to the process of association of two nucleic acid strands to form an antiparallel duplex stabilized by means of hydrogen bonding between residues of the opposite nucleic acid strands.

"Hybridizing" and "binding", with respect to polynucleotides, are used interchangeably. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, substantially similar conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature. Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

As used herein the term "isolated" is meant to describe a polynucleotide, a polypeptide, an antibody, or a host cell that is in an environment different from that in which the polynucleotide, the polypeptide, the antibody, or the host cell naturally occurs.

As used herein, the term "organelle" refers to cellular membrane-bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "host" or "organism" includes humans, mammals (e.g., cats, dogs, horses, etc.), living cells, and other living organisms. A living organism can be as simple as, for example, a single eukaryotic cell or as complex as a mammal.

General Discussion

Briefly described, embodiments of this disclosure, among others, include BRET systems, BRET fusion proteins, BRET vectors, mutated *Renilla* Luciferase proteins, and methods of studying cellular events. The BRET system can detect distance-dependent cellular events, such as, but not limited to, protein-protein interactions, protein dimerization, protein phosphorylation, caspase detection, and/or cellular ion exchange. In addition, the BRET system can be used to detect (and visualize) and quantitate cellular events in vitro as well as in vivo, which bridges the gap between the two types of studies.

In general, BRET systems involve the non-radiative transfer of energy between a bioluminescence donor molecule and a fluorescent acceptor molecule by the FORSTER mechanism. The energy transfer primarily depends on: (i) an overlap between the emission and excitation spectra of the donor and acceptor molecules, respectively and (ii) the proximity of about 100 Angstroms (A) between the donor and acceptor molecules. The donor molecule in BRET produces light via chemiluminescence, so it is amenable to small animal imaging. In addition, the BRET system does not use an external light excitation source, which provides potentially greater sensitivity in living subjects because of the low signal to noise ratio. In addition, the BRET system can include a detection system having a cooled charge-coupled device (CCD) camera capable of imaging low quantum yield of visible light ranges from 300 to 900 nm wavelength emitted from superficial and deep tissue structures of small living subjects.

As mentioned above, the BRET system can be used to detect (and visualize) and quantitate cellular events in vitro as well as in vivo studies, which decreases time and expenses since the same system can be used for cells and living organisms. The BRET system can test an event occurrence in a large number of protein samples, and has the capacity to transition from single cells to living animals without changing the imaging device. In addition, the BRET system can be used to detect (and visualize) and quantitate cellular events from a single cell or more.

The BRET system can non-invasively measure cellular events at a depth of about 2 cm or less in an animal. For example, the BRET system can be used to measure cellular events in deep tissue. The BRET system can measure the energy in cells in about 5 seconds to 5 minutes, typically 1 minute, but it should be noted that the acquisition time can vary depending, at least in part, on the cellular expression, strength of interaction, amount of luciferase substrate and the like. The BRET system can measure the energy emission in a living host (e.g., rat or mouse) in about 1 minute to about 10 minutes, but typically in about 3-5 minutes, but it should be noted that the acquisition time can vary depending, at least in part, on the cellular expression, strength of interaction, animal size, depth of interaction in the animal, amount of luciferase substrate, and the like.

In embodiments of the BRET system using the mutated *Renilla* Luciferase protein, a sensitivity increase of about 40 fold can be realized relative to unmutated *Renilla* Luciferase. Also in embodiments using the mutated *Renilla* Luciferase protein, the mutated *Renilla* Luciferase protein is more stable than the non-mutated *Renilla* Luciferase protein. Additional details regarding the mutated *Renilla* Luciferase protein are described below and in the Examples.

The present disclosure relates generally to methods for studying protein-protein interactions inside living organisms in which one can image in a living animal the interaction of two proteins and measure the degree of that interaction. This approach facilitates the study of protein-protein interactions to understand fundamental cell biology and will enable the in vivo testing of pharmaceuticals designed to modulate protein-protein interactions. The BRET system can be used in these embodiments in in vitro and/or in in vivo.

In another embodiment, protein-protein interactions in living animals are measured to determine the efficacy of drugs administered to modulate or block a protein-protein interaction. In another embodiment, drugs targeting protein-protein interactions may be optimized by administering the drugs to living animals having the protein-protein interaction system, monitoring any resultant signal change, and selecting drugs producing the desired response. The BRET system can be used in these embodiments in vitro and/or in vivo.

In other embodiments, the BRET system can be used in at least the following ways: as a sensor for programmed cell death from live cells and from living subjects; to monitor and assess signal transduction in living animals; to monitor and assess cellular ion influx in living animals; and to monitor and assess protein-protein interaction during development in a transgenic animal.

In another embodiment, a cell line or transgenic animal is marked with vector sets described herein that are developed utilizing coding regions for the two proteins of interest, followed by optical imaging to quantitate protein-protein interaction in the presence and absence of pharmaceuticals designed to modulate the interaction. As will be appreciated by the skilled practitioner, this technique will significantly accelerate drug validation by allowing testing in vivo. The BRET system can be used in these embodiments in vitro and/or in vivo.

BRET Systems and Methods of Use

In general, the BRET system includes, but is not limited to, a first fusion protein (BRET fusion protein), a second fusion protein (Fluorescent fusion protein), a bioluminescence initiating compound, and a detection system. The first fusion protein includes, but is not limited to, a first target protein and a bioluminescence donor molecule. The second fusion protein includes, but is not limited to, a second target protein and a fluorescent acceptor molecule. The first target protein and the second target protein are selected because there is interest in their interaction (or lack thereof) in a host (e.g., a cell or a living animal).

Each fusion protein can be encoded in a vector (e.g., or other expression system) including a polynucleotide having the appropriate nucleotide sequence. Methods of constructing polynucleotides are well known in the art. It should also be noted that the polynucleotide sequence will change depending, at least in part upon, the first and second proteins selected. Embodiments of this disclosure anticipate that numerous pairs of proteins can be selected and included in either the first fusion protein or the second fusion protein.

Once the first fusion protein and the second protein are in the host (e.g., expressed using a vector or other expression system known in the art encoding each fusion protein), the two fusion proteins can be monitored to determine if they interact, and the extent to which they interact (real time qualitative and quantitative measurement in vitro and/or in vivo).

When the first fusion protein and the second fusion protein are within less than about 50 to 100 Angstroms of one another and in the presence of the bioluminescence initiating compound, the bioluminescence initiating compound can react with the bioluminescence donor molecule. The reaction causes the bioluminescence donor molecule to emit bioluminescence energy. The energy is accepted by the fluorescent acceptor molecule of the second fusion protein, and then the fluorescent acceptor molecule emits fluorescent energy. The bioluminescence energy and the fluorescent energy can be detected and quantitiated in real time using a detection system. The strength of the signal corresponding to the bioluminescence energy and the fluorescent energy can be an indication of and/or degree of cellular interaction.

The detection system includes, but is not limited to, a light-tight module and an imaging device disposed in the light-tight module. The imaging device can include, but is not limited to, a CCD camera and a cooled CCD camera.

Charged coupled device (CCD) detectors are made of silicon crystals sliced into thin sheets for fabrication into integrated circuits using similar technologies to those used in making computer silicon chips. For a detailed overview of CCD technology, please refer to Spibey et al. (2001, Electrophoresis 22: 829-836).

One of the properties of silicon-based detectors is their high sensitivity to light, allowing them to detect light in the visible to near-infrared range. CCD cameras operate by converting light photons at wavelengths between 400 and 1000 nm that strike a CCD pixel with an energy of just 2-3 eV into electrons. A CCD contains semiconductors that are connected so that the output of one serves as the input of the next. In this way, an electrical charge pattern, corresponding to the intensity of incoming photons, is read out of the CCD into an output register and amplifier at the edge of the CCD for digitization. Older intensified CCD cameras had much lower sensitivities than newer-generation cooled CCD cameras. This is because thermal noise (termed "dark-current") from thermal energy within the silicon lattice of a CCD chip resulted in constant release of electrons. Thermal noise is dramatically reduced if the chip is cooled; dark current falls by a factor of 10 for every 20° C. decrease in temperature.

In the BRET system, the CCD camera is usually mounted in a light-tight specimen chamber, and is attached to a cryogenic refrigeration unit (for camera cooling about 20° C. to −150° C.). A camera controller, linked to a computer system, is used for data acquisition and analysis. An image is often shown as a color image that is superimposed on a gray-scale photographic image of the object (e.g., a small animal) using overlay and image analysis software. Usually a region of interest is manually selected over an area of signal intensity, and the maximum or average intensity is recorded as photons per second per centimeter squared per steradian (a steradian is a unit of solid angle). When the exposure conditions (including time, F/STOP, height of sample shelf, binning ratio, and time after injection with optical substrate) are kept substantially identical, the measurements are highly reproducible.

One advantage of optical bioluminescence imaging using the BRET system is that it can be used to detect very low levels of signal because the light emitted is virtually background free. It is quick and easy to perform and allows rapid testing of biological hypotheses and proofs of principle in living experimental models. It is also uniquely suited for high-throughput imaging because of its ease of operation, short acquisition times (typically 10-60 sec.), and large field of view (FOV) that enables measurement from all 96/384 wells of a 96/384 well plate and simultaneous measurement of up to six anesthetized living mice placed together (and even more mice in other embodiments). The CCD camera can be equipped with one or more filters. For example, 360-460 nm and 500-570 nm band pass emission filters can be used in embodiments of the BRET system. The same equipment can be easily adapted for measuring other known BRET systems (e.g., Rluc-YFP system) by installing emission filters to measure coelenterazine emission peak at 480 nm and YFP emission peak at 527 nm. The detection system can also be equipped with various zoom lenses to allow macroscopic enlargement and a close-up look to the samples (e.g., individual cells sitting on individual well plates). The height adjustable platform helps to focus the camera on the object while taking zoom action. The temperature controller of the platform helps to maintain accurate temperature requirements for samples (e.g., about 37° C. for maintaining animal body temperature, or a lower temperature (typically room temperature to 25° C.) for in vitro samples).

BRET Fusion Protein

As mentioned above, the BRET fusion protein includes, but is not limited to, a first target protein and a bioluminescence donor molecule. The bioluminescence donor molecule can include, but is not limited to, *Renilla* Luciferases, portions thereof, mutants thereof, variants thereof, and the like. In particular, the bioluminescence donor molecule can include, but is not limited to, a *Renilla* Luciferase protein (SEQ ID: No 1), double mutant (C124A/M185V) *Renilla* Luciferase proteins (e.g., SEQ ID: No 2), mutated *Renilla* Luciferase proteins (e.g., SEQ ID: No 3), variants of each, conservatively modified variants of each, and combinations thereof. In addition, the bioluminescence donor molecule can include, but is not limited to, other Luciferases or photoproteins such as, but not limited to, *Coleoptera* Luciferase, *Fierfly* Luciferase, *Gaussia* Luciferase, and aequorin photoproteinm Luciferase.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such emission maximum, quantum yield, brightness, and the like; in vivo and/or in vitro stability (e.g., half-life); and the like. Mutants can include single amino acid changes (point mutations), deletions of one or more amino acids (point-deletions), N-terminal truncations, C-terminal truncations, insertions, and the like. Mutants can be generated using standard techniques of molecular biology.

In an embodiment, the Luciferase mutants retain Luciferase activity (e.g., catalyze the conversion of a coelenterazine substrate into a luminescent product in the presence of molecular oxygen). In an embodiment, the Luciferase mutants have at least one of the following properties relative to their corresponding reference wild-type protein: modulated stability; enhanced light output; and/or modulated emission wavelength maximum, and modulated substrate utilization. In certain embodiments, the subject mutants include two or more of the above properties (e.g., modulated stability and enhanced brightness, enhanced light output and modulated emission maximum, modulated stability and modulated emission maximum, and the like.), or include three or more of the above properties (e.g., modulated stability, enhanced light output and modulated emission maximum).

As mentioned above, a mutated *Renilla* Luciferase protein (e.g., SEQ ID: No 3) can include, but is not limited to, 8 mutations in the sequence, and these include A55T, C124A, S130A, K136R, A143M, M185V, M253L, and S287L. In addition, mutated *Renilla* Luciferase proteins can include conservatively modified variants of one or more of these mutations as long as the conservatively modified variant retains the characteristics of the mutated *Renilla* Luciferase protein.

In general, the mutated *Renilla* Luciferase protein is very stable. Previous work has shown that a C124A mutation [C152A in Liu J and Escher A (1999)] increases the stability of RLuc. In order to further enhance the stability of RLuc, a number of mutations were explored on top of the C124A mutation. The combination of 8 favorable mutations including C124A generated a mutant *Renilla* Luciferase (RLuc8) (SEQ ID NO: 3) that exhibited a greater than 150-fold stability improvement in murine serum when compared to native Rluc (<1 hr versus >100 hr) and increased the sensitivity of the BRET system by about 20 to 60 fold and about 40 fold relative to native *Renilla* Luciferase (SEQ ID NO: 1). In addition to being more stable, RLuc8 also exhibited at least a 4-fold improvement in light output, along with a 5 nm red shift to its emission spectrum with respect to the native Rluc. The *Renilla* Luciferase protein and the mutated *Renilla* Luciferase protein are described in more detail in the Examples.

Coelenterazine 400a (DBC) suffers from low light output when used with the native Rluc. Comparing the Rluc and mutated Rluc activity, the results show that by using the native Coelenterazine analogue the fold differences are only 1.3 fold in the quantum yield and 5 fold in the total light output, whereas with the use of Coelenterazine 400a substrate the respective fold differences are about 32 fold and 60 fold. Therefore, the mutant *Renilla* shows improvement in light output by its better substrate utilization capacity. In the case of M185V, a portion of the increased light output can be explained by enhanced quantum yield, especially for the Coelenterazine 400a analog, which is due to it's location in the "cap", a domain often used for substrate specificity in the haloalkane dehalogenases. Interestingly, the C124A mutation appears to facilitate the M185V mutation, as C124A/M185V double mutation has a 2 fold better light output with this substrate compared to M185V alone.

Additional alternations to the *Renilla* Luciferase protein (SEQ ID NO: 1), individually or in combination of the mutated *Renilla* Luciferase proteins (e.g., SEQ ID NO: 2 and SEQ ID NO: 3), are described below.

In another embodiment, the mutants have at least modulated stability as compared to their corresponding reference wild type protein. Specifically, the mutants have at least modulated stability under in vivo conditions as compared by their corresponding reference wild type. For purposes of the present disclosure, modulated stability under in vivo conditions is determined by evaluating the activity of a given mutant and its corresponding reference wild type protein under mammalian (e.g., rat or mouse) serum conditions for a duration of time.

In certain embodiments, a given mutant exhibits enhanced stability, where the magnitude of enhancement may be at least about 50%, such as at least about 75% or more (e.g., by at least about 2-fold or more, such as by at least about 10-fold or more, by at least about 50-fold or more, by at least about 150-fold more, etc).

In representative embodiments in which the nucleic acids encode a mutant of *Renilla* Luciferase that exhibits enhanced stability, the mutant may include a point mutation at at least one of the following positions in SEQ ID NO: 1: A55; C124, S130; A143; M253, and S287. Specific point mutations of interest include, but are not limited to: A55T; C124A, S130A; A143M, M253L, and/or S287L. In those embodiments where the C124A mutation is present, the encoded mutant typically further includes at least one additional mutation, such as one or more of the above additional point mutations and/or one or more of the light output enhancing and/or emission wavelength maximum modulating mutations described in greater detail below. In certain embodiments, the mutant includes two or more of the above mutations, such as three or more, four or more or even all of the above mutations, where additional mutations may also be present as well.

In certain embodiments, a given mutant exhibits enhanced lability (i.e., decreased stability), where the magnitude of enhanced lability may be at least about 10%, such as at least about 25% or more, including at least about 50% or more, e.g., by at least about 2-fold or more, such as by at least about 10-fold or more, by at least about 50-fold or more, etc.

In representative embodiments in which the nucleic acids encode a mutant of *Renilla* Luciferase that exhibits enhanced lability, the mutant may include a point mutation at at least one of the following positions: Q235 and S257. Specific point mutations of interest include, but are not limited to: Q235A and S257G. In certain embodiments, the mutant includes both the above mutations, where additional mutations may also be present as well.

In representative embodiments, the mutants exhibit increased light output as compared to their corresponding reference wild type protein. Specifically, the mutants have at least enhanced light output with a given coelenterazine substrate as compared to their corresponding reference wild type. For purposes of the present disclosure, increased light output is determined by evaluating at least one of the kinetics and quantum yield of a given mutant using an appropriate assay.

In certain embodiments, these mutants exhibit at least increased kinetics (e.g., as determined using an appropriate assay), where the magnitude of the increase (as compared to a reference wild type protein) is, in representative embodiments, at least about 25%, such as at least about 50% including at least about 75% or more (e.g., at least about 2-fold or more, at least about 25-fold or more, at least about 50-fold or more, at least about 100-fold or more, etc.).

In certain embodiments, these mutants exhibit at least increased quantum yield for a given coelenterazine substrate, where the magnitude of the increase (as compared to a reference wild type protein) is, in representative embodiments, at least about 25%, such as at least about 50% including at least about 75% or more (e.g., at least about 2-fold or more, at least about 25-fold or more, at least about 50-fold or more, at least about 100-fold or more, etc.).

In embodiments of mutants of *Renilla* Luciferase that exhibit enhanced light output, the mutants may include a point mutation at at least one of the following positions: K136; M185 and/or S287. Specific point mutations of interest include, but are not limited to: K136R, M185V and/or S287L. In certain embodiments, the mutant includes two or more of the above mutations, such as all of the above mutations, where additional mutations may also be present as well.

In representative embodiments, the mutants provide at least a modulated emission wavelength maximum as compared to their corresponding reference wild type protein. Specifically, the mutants provide at least a modulated wavelength maximum for a given coelenterazine substrate as compared by their corresponding reference wild type. For purposes of the present disclosure, wavelength emission maximum is determined by an appropriate convenient assay.

In certain embodiments, a given mutant exhibits a blue shifted emission wavelength maximum, by which is meant that the wavelength of the emission maximum is reduced as compared to the reference wild type control, where the magnitude of blue shift may be at least about 5 nm, such as at least about 10 nm or more (e.g., by at least about 15 nm or more, such as by at least about 20 nm or more, etc.).

In representative embodiments in which the mutants of *Renilla* Luciferase exhibit an emission wavelength maximum shifted to shorter wavelengths of light (blue shifted), the mutant may include a point mutation in the substrate binding pocket (or enzymatic pocket). In certain embodiments, the point mutation is at at least one of the following positions: N53, A54, D120, W121, V146, F181, and/or F286. Specific point mutations of interest include, but are not limited to: N53Q, A54P, D120N, W121F, V146I, V146M, F181W, and/or F286Y. In certain embodiments, the mutant includes two or more of the above mutations, such as three or more, four or more, five or more, six or more, or even all of the above mutations, where additional mutations may also be present as well.

In certain embodiments, a given mutant exhibits an emission wavelength maximum shifted to longer wavelengths of light (red shifted), by which is meant that the wavelength of the emission maximum is increased as compared to the reference wild type control, where the magnitude of red shift may be at least about 5 nm, such as at least about 10 nm or more (e.g., by at least about 15 nm or more, such as by at least about 20 nm or more, etc.).

In representative embodiments in which the mutants of *Renilla* Luciferase exhibit a red shifted emission wavelength maximum, the mutant may include a point mutation in the substrate binding pocket (or enzymatic pocket). In certain of these embodiments, the point mutation is at at least one of the following positions: I159, I163, F181, F261, F262, and/or I223. Specific point mutations of interest include, but are not limited to: I159F, I159H, I159Y, I163H, I163W, I163Y, F181Y, F261W, F262W, F262Y, I223C, I223H, I223M, and/or I223Q. In certain embodiments, the mutant includes two or more of the above mutations, such as three or more, four or more, five or more, or even all of the above mutations, where additional mutations may also be present as well.

BRET Vector

The BRET vector can include, but is not limited to, polynucleotides that encode the BRET fusion protein (e.g., the *Renilla* Luciferase (Rluc), the mutated *Renilla* Luciferase (e.g., Rluc8), and other mutated *Renilla* Luciferase proteins) and/or degenerate nucleotide sequences thereof. Methods of producing vectors (e.g., viral and non-viral) and polynucleotides are well known in the art. It should be noted that the BRET fusion protein can be expressed using other expression systems and the BRET vector is merely an illustrative embodiment.

Fluorescent Fusion Protein

As mentioned above, the fluorescent fusion protein includes, but is not limited to, a second target protein and a fluorescent acceptor molecule. In general, fluorophores absorb electromagnetic energy at one wavelength and emit electromagnetic energy at a second wavelength.

Representative fluorescent acceptor molecules (fluorophores) can include, but are not limited to, sgGFP, sgBFP, BFP blue shifted GFP (Y66H), Blue Fluorescent Protein, CFP—Cyan Fluorescent Protein, Cyan GFP, DsRed, monomeric RFP, EBFP, ECFP, EGFP, GFP (S65T), GFP red shifted (rsGFP), GFP wild type, non-UV excitation (wtGFP), GFP wild type, UV excitation (wtGFP), GFPuv, HcRed, rsGFP, Sapphire GFP, sgBFP™, sgBFP™ (super glow BFP), sgGFP™, sgGFP™ (super glow GFP), wt GFP, Yellow GFP, YFP, semiconductor nanoparticles (e.g., quantum dots, raman nanoparticles) or combinations thereof.

Other representative fluorescent acceptor molecules (fluorophores) can include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs—AutoFluorescent Protein—(Quantum Biotechnologies); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; Bimane; Bisbenzamide; Bisbenzimide (Hoechst); bis-BTC; Blancophor FFG; BlancophorSV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson™; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; Chlorophyll; Chromomycin A; Chromomycin A; CL-NERF; CMFDA; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5™; Cy7™; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DilC18(5)); DIDS; Dihydorhodamine 123 (DHR); Dil (DilC18(3)); Dinitrophenol; DiO (DiOC18 (3)); DiR; DiR (DilC18(7)); DM-NERF (high pH); DNP; Dopamine; DTAF; DY-630-NHS; DY-635-NHS; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium lodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); S65A; S65C; S65L; S65T; SBFI; Serotonin; Sevron Brilliant Red 2B; Sevron Brilliant Red 4G; Sevron Brilliant Red B; Sevron Orange; Sevron Yellow L; SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodaminelsoThioCyanate; True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; YOYO-3, Sybr Green, Thiazole orange (interchelating dyes), or combinations thereof.

Fluorescent Vector

The fluorescent vector can include, but is not limited to, a polynucleotide that encodes the fluorescent fusion protein (e.g., the protein of interest and the mutant green fluorescent protein ($GFP^2$)) and degenerate nucleotide sequences thereof. Methods of producing polynucleotides and vectors (e.g., viral and non-viral) are well known in the art. It should be noted that the fluorescent fusion protein can be expressed using other expression systems and the fluorescent vector is merely an illustrative embodiment.

Bioluminescence Initiating Compound

The bioluminescence initiating compound can include, but is not limited to, coelenterazine, analogs thereof, and functional derivatives thereof. Derivatives of coelenterazine include, but are not limited to, coelenterazine 400a, coelenterazine cp, coelenterazine f, coelenterazine fcp, coelenterazine h, coelenterazine hcp; coelenterazine ip, coelenterazine n, coelenterazine O, coelenterazine c, coelenterazine c, coelenterazine i, coelenterazine icp, coelenterazine 2-methyl, benzyl-coelenterazine bisdeoxycoelenterazine, and deep blue coelenterazine (DBC) (described in more detail in U.S. Pat. Nos. 6,020,192; 5,968,750 and 5,874,304).

In general, coelenterazines are known to luminesce when acted upon by a wide variety of bioluminescent proteins, specifically Luciferases. Useful, but non-limiting, coelenterazines are disclosed in U.S. patent application Ser. No. 10/053,482, filed Nov. 2, 2001, the disclosure which is hereby incorporated by reference in its entirety. Coelenterazines are available from Promega Corporation, Madison, Wis. and from Molecular Probes, Inc., Eugene, Oreg. Coelenterazines may also be synthesized as described for example in Shimomura et al., Biochem. J. 261: 913-20, 1989; Inouye et al., Biochem. Biophys. Res. Comm. 233: 349-53, 1997; and Teranishi et al., Anal. Biochem. 249: 37-43, 1997.

Methods of Use

As mentioned above, the present disclosure relates generally to methods for studying (e.g., detecting, localizing, or quantifying) protein-protein interactions inside a host living cell, tissue, or organ, or a host living organism using the BRET system. For example, a living animal can be imaged using the BRET system to measure the interaction of two proteins and the degree of that interaction. This approach facilitates the study of protein-protein interactions to understand fundamental cell biology and will enable the in vivo testing of pharmaceuticals designed to modulate protein-protein interactions.

The BRET system can be used to measure and quantify protein-protein interactions in living animals to determine the efficacy of drugs administered to modulate or block the protein-protein interaction. Further, the BRET system can be used to measure the effects of drugs targeting protein-protein interactions. In addition, the BRET system can be used to optimize administering the drugs to living animals having the protein-protein interaction system as well as to monitor any resultant signal changes, and selecting drugs producing the desired response.

Furthermore, the BRET system can be used to: monitor and assess signal transduction in living animals; monitor and assess programmed cell death in living animals; monitor and assess cellular ion influx in living animals; and monitor and assess protein-protein interaction during development in a transgenic animal.

In another embodiment, a cell line or transgenic plant or animal is marked with vector sets described herein that are developed utilizing coding regions for the two proteins of interest, followed by optical imaging to quantitate protein-protein interaction in the presence and absence of pharmaceuticals designed to modulate the interaction. As will be appreciated by the skilled practitioner, this technique will significantly accelerate drug validation by allowing testing in vivo.

In this regard, transgenic animals comprise exogenous DNA incorporated into the animal's cells to effect a permanent or transient genetic change, preferably a permanent genetic change. Permanent genetic change is generally achieved by introduction of the DNA into the genome of the cell. Vectors for stable integration include plasmids, retroviruses and other animal viruses, YACS, and the like. Generally, transgenic animals are mammals, most typically mice.

The exogenous nucleic acid sequence may be present as an extrachromosomal element or stably integrated in all or a portion of the animal's cells, especially in germ cells.

Unless otherwise indicated, a transgenic animal comprises stable changes to the GERMLINE sequence. During the initial construction of the animal, chimeric animals (chimeras) are generated, in which only a subset of cells have the altered genome. Chimeras may then be bred to generate offspring heterozygous for the transgene. Male and female heterozygotes may then be bred to generate homozygous transgenic animals.

Typically, transgenic animals are generated using transgenes from a different species or transgenes with an altered nucleic acid sequence. For example, a human gene may be introduced as a transgene into the genome of a mouse or other animal. The introduced gene may be a wild-type gene, naturally occurring polymorphism, or a genetically manipulated sequence, for example having deletions, substitutions or insertions in the coding or non-coding regions. Such a transgene, when introduced into a transgenic animal or cells in culture, is useful for testing potential therapeutic agents known or believed to interact with a particular target protein implicated in a disease or disorder. Where the introduced gene is a coding sequence, it is usually operably linked to a promoter, which may be constitutive or inducible, and other regulatory sequences required for expression in the host animal.

Transgenic animals can be produced by any suitable method known in the art, such as manipulation of embryos, embryonic stem cells, and the like. Transgenic animals may be made through homologous recombination, where the endogenous locus is altered. Alternatively, a nucleic acid construct is randomly integrated into the genome. Vectors for stable integration include plasmids, retroviruses and other animal viruses, YACS, and the like.

Numerous methods for preparing transgenic animals are now known, and others will likely be developed. See, e.g., U. S. Pats. Nos. 6,252,131, 6,455,757, 6,028,245, and 5,766, 879, all incorporated herein by reference. Any method that produces a transgenic animal expressing a reporter gene following complementation or reconstitution is suitable for use in the practice of the present invention. The microinjection technique is particularly useful for incorporating transgenes into the genome without the accompanying removal of other genes.

The transgenic animals described herein may be used to identify compounds affecting protein-protein interactions and thus useful in the treatment of those pathologies associated with particular protein interactions. For example, transgenic animals comprising split reporter genes may be treated with various candidate compounds and the resulting effect, if any, on reporter gene expression, as, for example, resulting from blocking or modulating complementation or reconstitution of the reporter gene, evaluated.

As will be appreciated by one of skill in the art, such screening may also be done in cell culture. Preferably, the compounds screened are suitable for use in humans.

The subject animals may be used by themselves, or in combination with control animals.

Transgenic plants may be produced in a similar manner. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants are also reviewed in Plant Biochemistry and Molecular Biology (eds Lea & Leegood, John Wiley & Sons) (1993) pp 275-295.

Kits

This disclosure encompasses kits, which may include, but are not limited to, a BRET fusion protein, a BRET vector, a fluorescent fusion protein, a fluorescent vector, a bioluminescence initiating compound, a test drug, and directions (written instructions for their use). The components listed above can be tailored to the particular cellular event to be monitored (e.g., protein-protein interaction). The kit can further include appropriate buffers and reagents known in the art for administering various combinations of the components listed above to the host cell or host organism.

EXAMPLES

Now having described the embodiments of the BRET system, in general, examples 1 and 2 describe some additional embodiments of the BRET system. While embodiments of the BRET system are described in connection with examples 1 and 2 and the corresponding text and figures, there is no intent to limit embodiments of the BRET systems to these descriptions. On the contrary, the intent is to cover all alternatives, modifications, and equivalents included within the spirit and scope of embodiments of the present disclosure.

Example 1

This example demonstrates a significant advancement of imaging of a distance-dependent physical process known as bioluminescent resonance energy transfer (BRET) signal in living subjects, by using a cooled charge coupled device (CCD) camera. A CCD camera-based spectral imaging strategy enables simultaneous visualization and quantitation of BRET signal from live cells and cells implanted in living mice. A BRET system as described herein is used, which utilizes Renilla Luciferase (hRluc) protein and its substrate DeepBlueC (DBC) as an energy donor, and a mutant green fluorescent protein (GFP2) as the acceptor. In this example, the donor and acceptor proteins were fused to FKBP12 and FRB, respectively, which are known to interact only in the presence of the small molecule mediator rapamycin. Mammalian cells expressing these fusion constructs were imaged using a cooled-CCD camera either directly from culture dishes or by implanting them into mice. By comparing the emission photon yields in the presence and absence of rapamycin, the specific BRET signal was determined. The CCD imaging approach of BRET signal is particularly appealing due to its capacity to seamlessly bridge the gap between in vitro and in vivo studies. This example illustrates embodiments of the BRET system as a powerful tool for interrogating and observing protein-protein interactions directly at limited depths in living mice, for example.

Introduction

The interaction of specific cellular proteins forms the basis for many important biological processes including various signal transduction and hormone activation pathways involved in tumorigenesis and metastasis. The ability to observe these interactions in the context of a living subject is crucial for understanding physiological factors that affect them. Several approaches have been developed for studying protein-protein interactions in cells. The yeast two-hybrid (Y2H) system uses inducible expression of a reporter gene as a method for indirectly monitoring protein-protein interaction. This approach is limited in that the interaction must occur in the nucleus of the cell. In split-reporter approaches, a reporter protein is complemented or reconstituted when two proteins interact. However, split reporter-based systems can lack sufficient sensitivity, as the complemented reporter activity is much lower in comparison to the intact reporter protein. Split complementation strategies also suffer in providing in-depth knowledge of the interacting proteins in terms of their proximity and real time measurements.

Fluorescence Resonance Energy Transfer (FRET) and Bioluminescence Resonance Energy Transfer (BRET) technology involves the non-radiative transfer of energy between the donor and acceptor molecules by the FORSTER mechanism, which are well adapted for studying protein-protein interactions and protein dimerizations, but generally reserved for such measurements from cell lysates or intact cells using a microplate reader. Resonance energy transfer (RET)-based techniques determine protein-protein interaction, with information on the proximity of the donor and acceptor molecules. BRET/FRET also elucidates information on real time kinetics of the interacting partners. FRET involves fluorescent molecules each as donor and acceptor molecules, allowing sensitive detection and microscopic visualization of protein interactions and intracellular signaling events in living cells.

Unlike FRET, BRET technology involves a bioluminescence and a fluorescence molecule as an energy donor and acceptor respectively. Because the donor molecule in BRET produces light via chemiluminescence, it is more amenable to small animal imaging. One significant advantage of BRET over FRET is that as no external light excitation is required in BRET, it can result in greater sensitivity in living subjects because of a higher signal to background ratio.

Figure 1B:
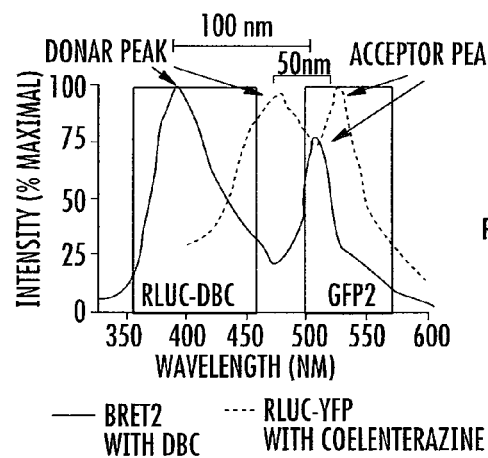
FIG. 1B illustrates a diagram explaining the emission spectral properties of two distinct BRET systems. The dashed line represents the YFP and RLUC emission curve showing that the spectral resolution between donor and acceptor emission wavelength is about 50 nm. The solid line represents the GFP$^2$ and RLUC emission curve showing that the improved spectral resolution is about 100 nm. The rectangular color zones represent the wavelength range covered by the BRET$^2$ specific band pass emission filters as marked.

BRET measurements are currently done using a microplate reader equipped with specific filter sets for detection of the donor and acceptor emission peaks. In this example, using a cooled CCD camera imaging system, a BRET assay and system can be performed on cell lysates, live cells, and from certain depths of living animals (e.g., utilizing a BRET$^2$ (RLUC and GFP$^2$) system). A CCD imaging approach of BRET signal measurement is particularly appealing due to its capacity to seamlessly bridge the gap between in vitro and in vivo studies. The BRET system disclosed herein, using the Deep Blue coelenterazine (DBC) substrate, achieves spectral resolution of about 100 nm (FIG. 1B). This wide spectral separation between the donor and acceptor emission light is helpful for selecting the component light signals from living subjects. Less photo-bleaching of $GFP^2$ over YFP is also considered to be another important parameter for using the BRET system.

Figure 1C:
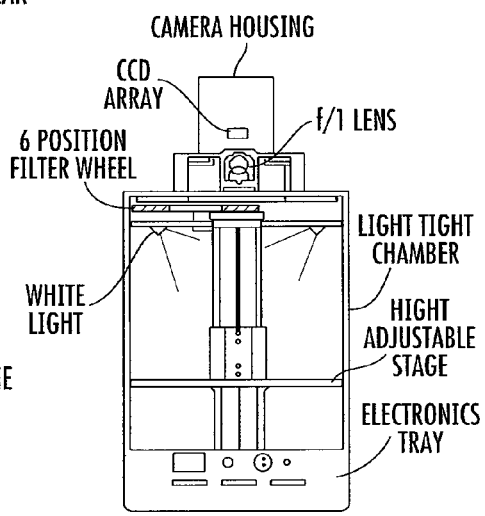
FIG. 1C illustrates a diagram of an embodiment of a black box cooled CCD imaging apparatus (Xenogen) that has been used to measure BRET signals from both live cells as well as cells from within living mice. The 6-position filter wheel was equipped with BRET specific DBC donor emission and GFP$^2$ acceptor emission filters. Cells in culture plate or implanted in living mice can be placed on the height-adjustable stage, and the donor and acceptor component lights can be captured using the highly sensitive CCD camera located on the top of the box. The white light sources allow for obtaining a grey scale photograph of the subject on which to superimpose light signals from within the subject due to BRET.

Considering these specifications as well as others, this example uses a BRET system to achieve better sensitivity while using a cooled CCD imaging device. The BRET system was tested using the human proteins FKBP12 (FKBP, for FK506 binding protein) and a 93 amino acid portion of FRAP called FRB (mTOR kinase rapamycin binding domain), which are known to have strong interaction in the presence of a small mediator molecule rapamycin. In the presence of rapamycin, the two fusion proteins dimerize, and therefore bring the BRET partners in close proximity allowing RET to occur (FIG. 1A). Further, the quantitative photon outputs were established from CCD imaging system (FIG. 1C), which can be used for determining the BRET ratio from live cells. (Note that FKBP12-hRluc and $GFP^2$-FRB refer to the fusion genes whereas FKBP12-RLUC and $GFP^2$-FRB refer to the fusion proteins.)

Results

Figure 3A:
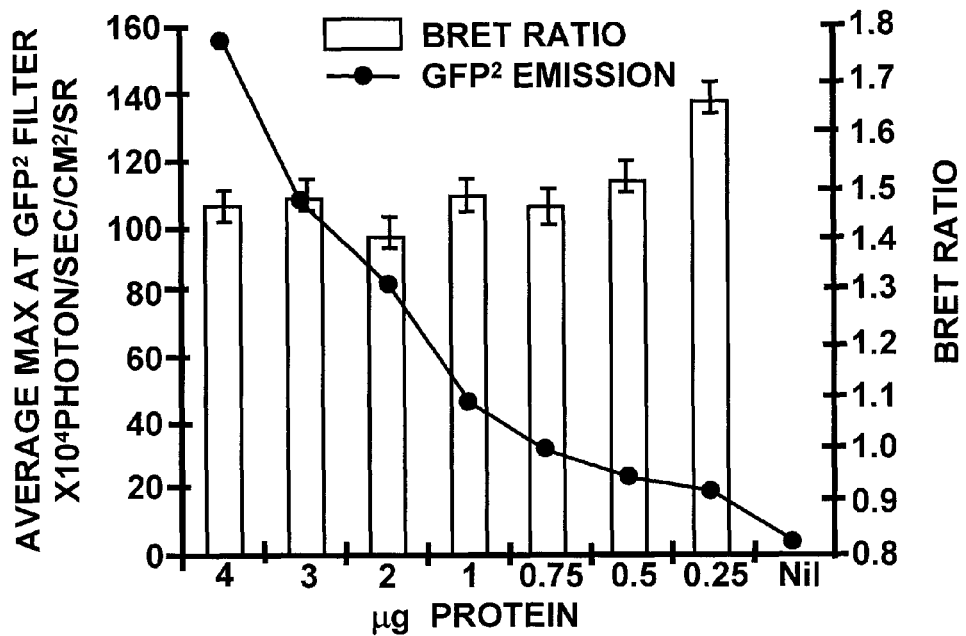
FIGS. 3A through 3C illustrate the visualization and quantitation of BRET time kinetics from live cells using a cooled CCD camera.
Figure 3B:
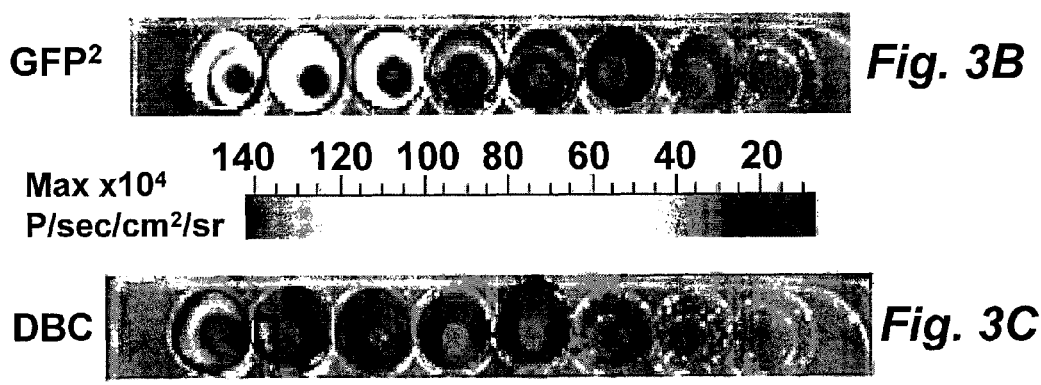

BRET signal shows linearity as a function of protein content and time and can be detected in as few as 30 cells using a cooled CCD camera: BRET assays were first performed with serially diluted total proteins isolated from 293T cells at 24 hours after being transiently transfected with $pBRET^2$ and phRluc plasmids along with 1/10th amount of CMV-Fluc plasmid as transfection control. For BRET expressing cells, $GFP^2$ signal shows a linear increase with the total protein quantity added in each well (FIG. 2). Based on the average radiance (Max) obtained by drawing ROI over the appropriate wells, the $BRET^2$ ratio was established to be on average 1.5 at each protein concentration used. Next, component light signals were imaged over time (at each alternate minute for 15 minutes) directly from fixed number of 293T cells in well plates transfected with either $pBRET^2$, phRluc plasmid or non-transfected cells with added DBC (FIG. 3A-B). On the $pBRET^2$ plasmid transfected wells using $GFP^2$ filters, the average radiance at one minute is $98.16\pm2.2\times10^4$, which gradually decreases to a value of $51.05\pm0.8\times10^4$ over 15 minutes. Using a DBC filter, $pBRET^2$ plasmid transfected well at one minute yields average radiance of $74.47\pm1.89\times10^4$, which gradually decreases to a value of $42.7\pm1.9\times10^4$ over 15 minutes. The DBC filter time kinetics was fit to a mono-exponential to determine the decay factor, the value of which was used in further studies (data not shown). The background average radiance was determined as $1.96\pm0.2\times10^4$ and $2.02\pm0.7\times10^4$ using $GFP^2$ and DBC filter respectively on the wells with non-transfected 293T cells with added DBC.

Figure 3C:

By applying the background subtracted values to the standard formula for a BRET ratio calculation as [{Emission @500-570-Emission @360-460×(Emission of RLUC @500-570/Emission of RLUC @360-460)}/mission @360-460], the average BRET ratio was determined to be about 1.3 for $pBRET^2$, which remains unchanged at each time points of CCD measurements. Further, to determine the least number of cells that can be imaged using the CCD camera approach, serially diluted $pBRET^2$ and phRluc transfected 293T cells in individual wells of a 96 well plate were used and imaged using a zoom lens. The results show that individual cells from well plates can be spectrally resolved by the cooled CCD camera and as few as 30 cells per well were visualized successfully using each filter (FIG. 3C).

Interactions between FKBP12 fused to the N-terminus of hRluc and FRB fused to the C-terminus of $GFP^2$ yield detectable $BRET^2$ signal in the presence of rapamycin: Donor (hRluc) and acceptor ($GFP^2$) DNA with and without interacting proteins cloned in different combinations were transfected in 293T cells and checked for expression of the intact fusions by western blotting (not shown) using either Renilla or living color peptide antibody for $GFP^2$ expression. Cells co-transfected with pFKBP12-hRluc and pGFP-FRB in presence of rapamycin show the highest signal, with an average radiance of $39.12\pm0.66\times10^4$ on the $GFP^2$ filter and $26.4\pm1.71\times10^4$ on the DBC filter (FIG. 4A-B). Wells transfected with the same combination of plasmids with a similar DNA ratio but not incubated with rapamycin imaged simultaneously using the $GFP^2$ filter yields average radiance of $8.73\pm1.52\times10^4$. Average radiance obtained from pFKBP12-hRluc transfected wells with rapamycin using the DBC filter is $25.42\pm1.31\times10^4$. The $BRET^2$ ratio from FKBP12-FRB interaction is estimated as 1.04, indicating a strong interaction between the two proteins. The same experiments in N2a cell lines lead to similar results (data not shown). The results also show that in presence of rapamycin, RLUC-DBC photon emission is lower in comparison to the cells not incubated with rapamycin (FIG. 4A). To determine the optimum rapamycin concentration for obtaining highest $BRET^2$ signal, the use of 320 nM rapamycin shows saturation of the $BRET^2$ signal (FIG. 4C). This concentration of the drug being close to the $IC^{50}$ value, we determine 160 nM of concentration to be optimum for obtaining significant BRET signal. Therefore, 160 nM rapamycin was used as the optimum dose in all cell culture experiments.

To elucidate the dynamic nature of the BRET system, 293T cells co-transfected with pFKBP12-hRluc and $pGFP^2$-FRB were repeatedly imaged by adding and withdrawing rapamycin in succession at different time points from the incubating medium. As control, the same transfected cells were constantly maintained in rapamycin containing media. The result shows that a $BRET^2$ ratio shifts from 0.29 at 24 hours to 1.16 at 30 hours. Once rapamycin is added in the medium, it takes about 40 hours to have the $BRET^2$ ratio come down to 0.17 in rapamycin free condition. At this time point (70 hours), the cells treated with rapamycin for 8 hours showed a gain in the $BRET^2$ ratio of 0.79 (FIG. 4D) signifying occurrence of BRET.

Figure 5A:
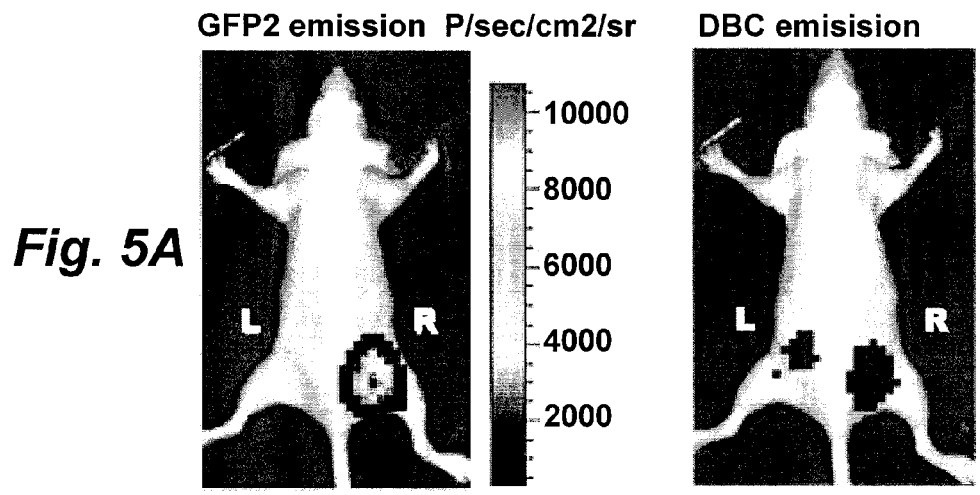
FIGS. 5A through 5C illustrate in vivo imaging of BRET$^2$ signals from living mice.
Figure 5B:
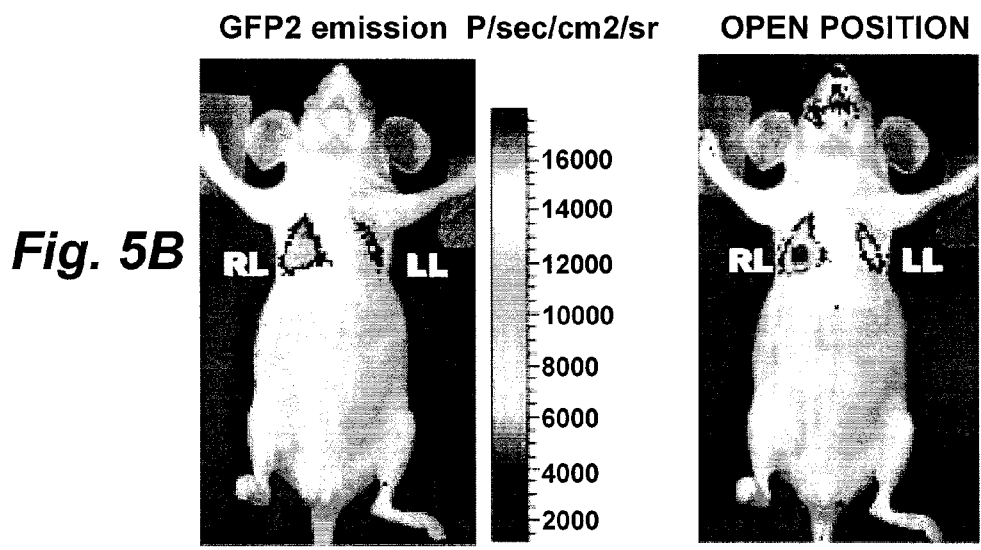
Figure 5C:
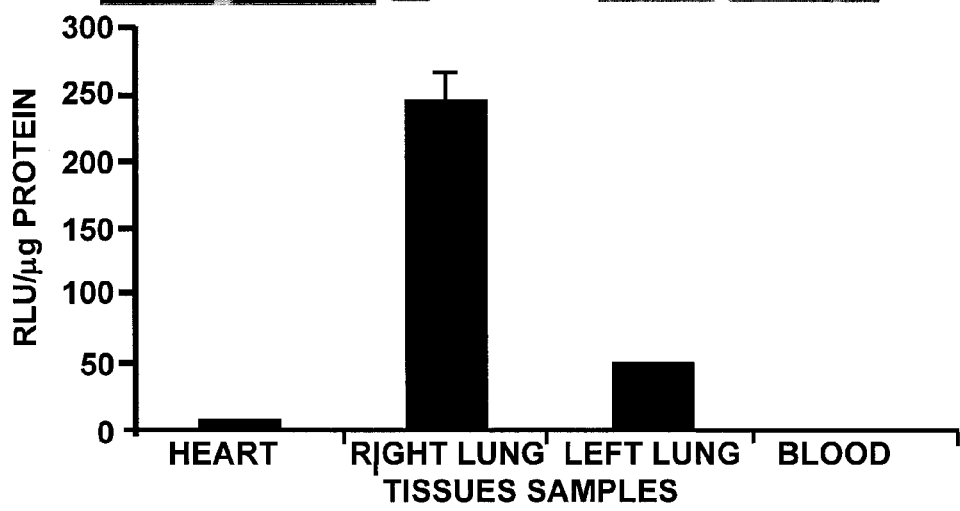

A CCD camera can be used for non-invasive monitoring of $BRET^2$ specific $GFP^2$ signal from living mice: Following cell culture studies, live animal non-invasive imaging of $BRET^2$ signal from subcutaneous (s.c.) tissue-depths as well as from deeper tissues was performed. Implanting $3\times10^6$ 293T cells transiently transfected with $pBRET^2$ and phRluc plasmids at sub-cutaneous tissue depths, the average radiance for $pBRET^2$ expressing cells is $11.8\pm0.9\times10^3$, in comparison to $0.342\pm0.031\times10^3$ from RLUC expressing cells on $GFP^2$ filter (FIG. 5A). Further, repeated scanning of the same animals using the $GFP^2$ filter over 15 minutes time period show Max value markedly drops, which reflects that $GFP^2$ light kinetics follow the fast light kinetics of RLUC-DBC (not shown). Further, to verify the possibilities of detecting component light signals from greater tissue depths, $4\times10^6$ 293T $BRET^2$ expressing cells were injected via tail vein followed by delivering a higher dose of DBC substrate. These results show that 25 μg DBC is not enough to visualize specific lung signal, but $GFP^2$ specific component light can be seen with an increased DBC dose of 100 μg (FIG. 5B). Average radiance obtained at GFP$^2$ filter collected for 1-5 minutes from cells trafficked to the lungs is 9.67±2.11×10$^4$, in comparison to a background value from lower abdomen is 1.78±0.3×10$^4$. By turning the filter wheel to DBC, no RLUC-DBC emission light was obtained from lungs of the same animal between minutes 5-10. However, scanning at 10-15 minutes using the open filter position to capture total light, confirmed specific signals from lungs. These results were further verified by performing a RLUC protein assay from thoracic organs of the same animal as shown in FIG. 5C.

CCD imaging allows RET signal detection from specific protein-protein interactions from small animals with transient and stable cellular expression of reporters. For the protein-protein interaction experiment, cooled CCD camera imaging of mice (n=4) that were implanted with transiently transfected 293T cells expressing BRET$^2$, FKBP12-RLUC and both FKBP12-RLUC and GFP$^2$-FRB, which also received rapamycin (5 mg/kg) systemically (36), show average radiance on the respective sites as 24.6±4.1×10$^4$, 1.22±3.2×10$^4$ and 7.84±1.9×10$^4$ on GFP$^2$ filter (FIG. 6). The other set of mice (n=3) that were implanted with the same cells, but didn't receive rapamycin show average radiance of 79.82±11.2× 10$^3$, 5.81±1.77×10$^3$ and 13.46±4.9×10$^3$ respectively using GFP$^2$ filter. These results clearly indicate that mice that received rapamycin in vivo produce specific GFP$^2$ signal in the appropriate locations, indicating occurrence of BRET.

To minimize transfection variability, stable N2a (rat neuroblastoma) and A375M (human melanoma) cells were established, which constitutively over-express FKBP12-RLUC fusion protein by selecting against neomycin resistance gene. Then the BRET$^2$ ratio for these lines were established by transfecting or not with pGFP$^2$-FRB in presence or absence of rapamycin (data not shown). CCD camera imaging of nude mice implanted with 5×10$^6$ N2a cells stably expressing FKBP12-RLUC alone showed average radiance of 1.68±0.3×10$^3$, whereas cells that also express GFP$^2$-FRB fusion showed average radiance as 21.59±4.9×10$^3$ on GFP$^2$ filter, indicating BRET occurrence (image not shown). Follow-up scan on DBC filter of the same mice showed the average radiance from the corresponding locations as 3.97±0.7×10$^3$ and 3.65±0.8×10$^3$ respectively, indicating an equal number of cells.

Discussion

To date, several techniques have been developed for studying protein-protein interactions in cell culture and in small living subjects. Development of BRET systems including cooled CCD imaging systems to quantify optical reporter signals from specific enzyme-substrate reactions has resulted in many possibilities for non-invasive monitoring of reporter gene expression from live cells as well as from live animals. This technology is very useful for fast screening by visualizing gene expression from cultured cells and live animals in a short time span at relatively low cost. The current work is the first demonstration of the BRET system including the cooled CCD imaging that has been utilized to measure component light signals in determining protein-protein interactions using a BRET$^2$ assay in intact cells or living small subjects. This example shows that quantitative BRET imaging is possible from cell lysates, live cells in culture, and semi-quantitatively from limited depths in small animals by performing relatively simple modifications to the BRET system, including the CCD imaging device.

CCD imaging with control pBRET$^2$ plasmid yields an average BRET$^2$ ratio of 1.4, which is close to the value of ~1.2 as is obtained by using a Fusion™ microplate reader. The BRET$^2$ ratio value varies with other brand products of microplate readers due to variable sensitivity of the photo-multiplier tubes. Cell imaging of as few as 30 cells could be collectively imaged and spectrally resolved for the BRET system for specific component light signals. Further, the number of cells stably expressing the plasmid that can be detected using the same methodology is much higher. The BRET system was used to study small molecule rapamycin mediated hetero-dimerizations of two human proteins FRB and FKBP12 using various cell lines and to non-invasively image the signal from living mice. The BRET ratio was determined to be about 1.04 from rapamycin-mediated FKBP12-FRB interaction in mammalian cells in culture. This ratio is closer to the value of the control BRET construct, thereby reflecting relatively strong interaction between these two human proteins. It was observed that rapamycin itself absorbs some of the photons in the assay, as evidenced by a drop in hRLUC signal in the presence of rapamycin. Control scans for Fluc signal output clearly shows that this decrease in DBC signal is not due to rapamycin mediated cell death. The GFP$^2$ signal was quantified under these conditions, which allowed the BRET$^2$ signal to be further analyzed. Further, to demonstrate that cooled CCD imaging can truly reflect the dynamic nature of resonance energy transfer based techniques, repeated scanning was performed over time by adding or withdrawing the modulator drug rapamycin from the cell culture medium and demonstrated signal modulation. In this example, it is also demonstrated that the BRET system including the cooled CCD camera can be used to detect BRET signal directly from living mice. Both RLUC-DBC and GFP$^2$ signal from superficial tissues were detected, and BRET$^2$ specific GFP$^2$ signals from deeper sites were detected. With the current version of the BRET$^2$ donor with blue-shifted emission wavelength, the luminescent light from deep tissues was not detected by the cooled CCD camera. The use of hRluc mutant with increased photon yields and use of a new BRET partner that has further red-shifted emission light pattern might be useful in detecting emissions from deeper tissues. In addition, the use of quantum dots as acceptors may allow for novel molecular imaging probes with red-shifted emission wavelengths for use in living subjects. The determination of the BRET$^2$ ratio from animal subjects depends on various issues like the donor and acceptor emission wavelength, tissue density, and hemoglobin concentration.

The evaluation of small molecule mediated protein-protein interactions can be relatively efficient and unproblematic in cell culture, even when exposing the cells to low concentrations of the drug. However, similar investigations in a living animal model could depend on many factors including the availability of an efficient and sensitive reporter system and a highly sensitive imaging modality to help achieve detectable signals. In addition, the compounds under investigation preferably one able to circulate in the vascular compartment with enough concentration and for a suitable period to permit sufficient quantities to reach the target site. This in turn, would allow sufficient interactions to occur at the target. In the present example, both transient and stably expressing cells were used for mouse studies. Significant enhancement of the BRET$^2$ signal was achieved from animals where cells were pre-incubated with rapamycin before implantation. Significant BRET$^2$ specific signal was also observed in animals with higher number of subcutaneous cell implants where 5 mg/kg rapamycin was delivered systemically. It is likely that the dosage level of the drug and/or the time allowed for the drug to reach the target cells might affect results of these experiments. One of skill in the art should be able to screen new dimerizer drugs for known or unknown protein interactions from superficial tissues. Establishment of long-term tumors using stably transfected cells of both protein partners would likely improve the result by increasing the blood supply to the engrafted cells, helping consequent improvement in imaging BRET$^2$ signal.

Methods and Materials

Materials: pBRET², phRluc-N3 and pGFP²-C3 plasmids and Deep Blue Coelenterazine were purchased from Perkin Elmer (former BioSignal Packard, Montreal, Canada). BRET specific 360-460 nm (DBC) and 500-570 nm (GFP²) filters were obtained from Omega. The Black box CCD imager used for this study is from Xenogen corp (Alameda, Calif.). Rapamycin (cat #R0395) was purchased from Sigma. Superfect transfection reagent was purchased from Qiagen. The dual Luciferase assay kit was purchased from Promega. D-PBS and all cell culture media were obtained from Invitrogen (formerly GIBCO). 3-4 weeks old nude mice (nu/nu) were obtained from Charles river laboratory.

Plasmid constructs: pBRET² (GFP²-MCS-hRluc) plasmid was used as control BRET vector. pGFP²-C3 and phRluc-N3 plasmid vectors were used for cloning FRB and FKBP12 nucleotide sequences. PCR amplified products of FRB and FKBP12 coding sequences were cloned in various combinations using suitable restriction enzyme sites to obtain the fusion constructs used in this study. All PCR amplified products were sequenced to match the template DNAs. Clonal selection was performed on bacto-agar plate using either zeomycin (for pBRET² and pGFP²-C3 vectors) or kanamycin (for phRluc-N3 vector) antibiotics.

Cell Culture: Three cell lines were used during this study. Human 293T embryonic kidney cells (ATCC, Manassas, Va.) were grown in MEM supplemented with 10% FBS and 1% penicillin streptomycin solution. The N2a cells obtained from V. P. Mauro (Scripps Research Institute, La Jolla, Calif.), and the A375 cells from M. Kolodney (Dept of Dermatology, UCLA, Los Angeles, Calif.) were grown in DMEM (high glucose) supplemented with 10% FBS and 1% penicillin streptomycin.

Cell Transfection, Clonal Isolation and Luciferase Assay: Fixed numbers of cells were plated in 24-well plates in natural growth media. Transient transfection was performed 24 hours later using Superfect reagent. Each transfection mix consisted of 1 µg of experimental plasmid along with 0.1 µg of pCMV-Fluc plasmid as transfection control. Total 1 µg/well of the pFKBP12-hRluc and pGFP²-FRB were co-transfected along with 0.1 µg Fluc plasmid. Three hours after transfection, the mix was removed and fresh media were added. Rapamycin was added to the appropriate wells at 160 nM concentration unless otherwise mentioned and the cells were incubated at 37° C. in $CO_2$ incubator for 24 hours before scans were performed. For isolating stably expressing FKBP12-RLUC clones, G418 selection was done using a concentration of 750 µg/ml for A375 cells and 600 µg/ml for N2a cells. The cells were harvested and assayed for RLUC activity using the Dual-Reporter Luciferase Assay System and a luminometer (Lumat 9507; Berthold, Nashua, N.H.) with 10 sec integration time.

Western blotting: Fusion plasmids constructed for these studies were checked for protein expression using 293T cells. 24 hours post-transfection, cells were harvested and lysed on ice using cell lysis buffer (Cell signaling). Estimated equal amount of the lysates were loaded in 10% Tris-HCl readygel (Bio-Rad) and transferred onto nitrocellulose membrane (Amersham). The blots were probed with either *Renilla* monoclonal antibody (Chemicon) or with Living color A.V. peptide antibody (Clonetech) to detect RLUC or GFP² fusions, respectively. α-tubulin monoclonal antibody (Sigma) was used as loading control.

In vitro BRET² Assay: For BRET² imaging and ratiometric calculations, 24 hrs post-transfection the culture media were removed from 24 well plates, washed with D-PBS, and then added with fresh 75 µl of D-PBS. Just before CCD imaging, 75 µl of diluted DBC (1 µg DBC/well final concentration in 24 well format) was added in each well and placed inside the black box CCD imaging system (tested with models IVIS100 and IVIS200) (Xenogen, Calif.). All scans were performed in luminescent mode, with one-minute integration time at binning 5, field of view (FOV) 25 cm, and stage temperature maintained at 26° C. unless otherwise mentioned. The filter wheel of the CCD imager was equipped with a 500-570 nm band pass emission filter for GFP² signal detection and a 360-460 nm band pass emission filter for RLUC-DBC signal detection. An hour later, FLUC signal was collected from individual wells by adding 0.1 µg D-luciferin substrate per well. For single cell imaging using a zoom lens the FOV was manually adjusted to 9.4 cm by raising the platform. Images were analyzed using LIVING IMAGE v2.5 software (Xenogen, Calif.). For quantification, regions of interests (ROI) were drawn over the respective wells as can be visualized from the photographic image overlaid on the luminescent image, and average Radiance (photons/sec/cm²/steradian) were computed using the software tools.

In Vivo Animal Imaging of BRET² Expression by Using a Cooled CCD Camera: 293T cells transiently transfected with either phRluc or pBRET² were harvested 24 hours post-transfection and resuspended in PBS. An aliquot of 3×10⁶ cells each was injected s.c. in a set of 3 anesthetized (ketamine: xylazine 4:1) nude mice. One hour after cell injection, 20 µg/mouse of DBC diluted in D-PBS (100 µl total volume) was injected via tail vein (i.v.) and imaged immediately using the CCD camera. For the deep tissue signal detection experiment, 3×10⁶ cells each were injected intravenously in another set of anesthetized nude mice, and a scan was performed half an hour later after 100 µg/mouse of DBC injection. For protein-protein interaction experiments, 293T cells were transiently transfected with either pBRET², pFKBP12-hRluc alone or co-transfected with pFKBP12-hRluc and pGFP²-FRB in 1:1 DNA ratio. The cells were harvested 24 hours post-transfection and re-suspended in PBS after counting the cell number. An aliquot of 5×10⁶ cells each was injected s.c. in a set of 6 nude mice. Three of these mice were kept aside, while the other 3 mice received single dose of 5 mg/kg rapamycin intra-peritonially (i.p.). After 7 hours, mice were injected intravenously with 25 µg of DBC/mouse and imaged using specified filters. For additional experiments, 5×10⁶ N2a clonal cells selected for stable FKBP12-hRLUC expression, as well as the same cells transiently transfected with pGFP²-FRB DNA, were s.c. implanted on nude mice and imaging was performed following the same procedure. The animals were placed supine in a light-tight chamber, and a gray-scale photographic reference image was obtained under low-level illumination. Photons emitted from implanted cells on mice were collected and integrated for a period of 5 minutes using specific filter sets.

Statistical Testing: Average radiance values obtained from both cell culture assays and in vivo mouse experiments by drawing ROI were used for BRET² ratiometric calculations using the formula shown in the result section. All cell culture and mouse group comparisons were performed with a Student's t test using Microsoft EXCEL. Values of $P \leq 0.05$ were considered statistically significant.

Example 2

Novel donor mutation enhances sensitivity for non-invasive imaging of bioluminescence resonance energy transfer signal in living subjects:

Introduction: This example demonstrates construction and validation of BRET vectors by fusing novel *Renilla* luciferase (RLuc) mutants (donor), selected for increased quantum yield and stability to the GFP² acceptor.

Methods: Three different mutations of RLuc, a single mutation C124A, a double mutation C124A/M185V, and a combination of eight mutations called RLuc8, were fused with GFP² and tested in HT1080 fibro-sarcoma cells by using CCD camera based spectral imaging. The new vectors were also tested in a small animal tumor model with implanted cells at various tissue depths.

Figure 7:
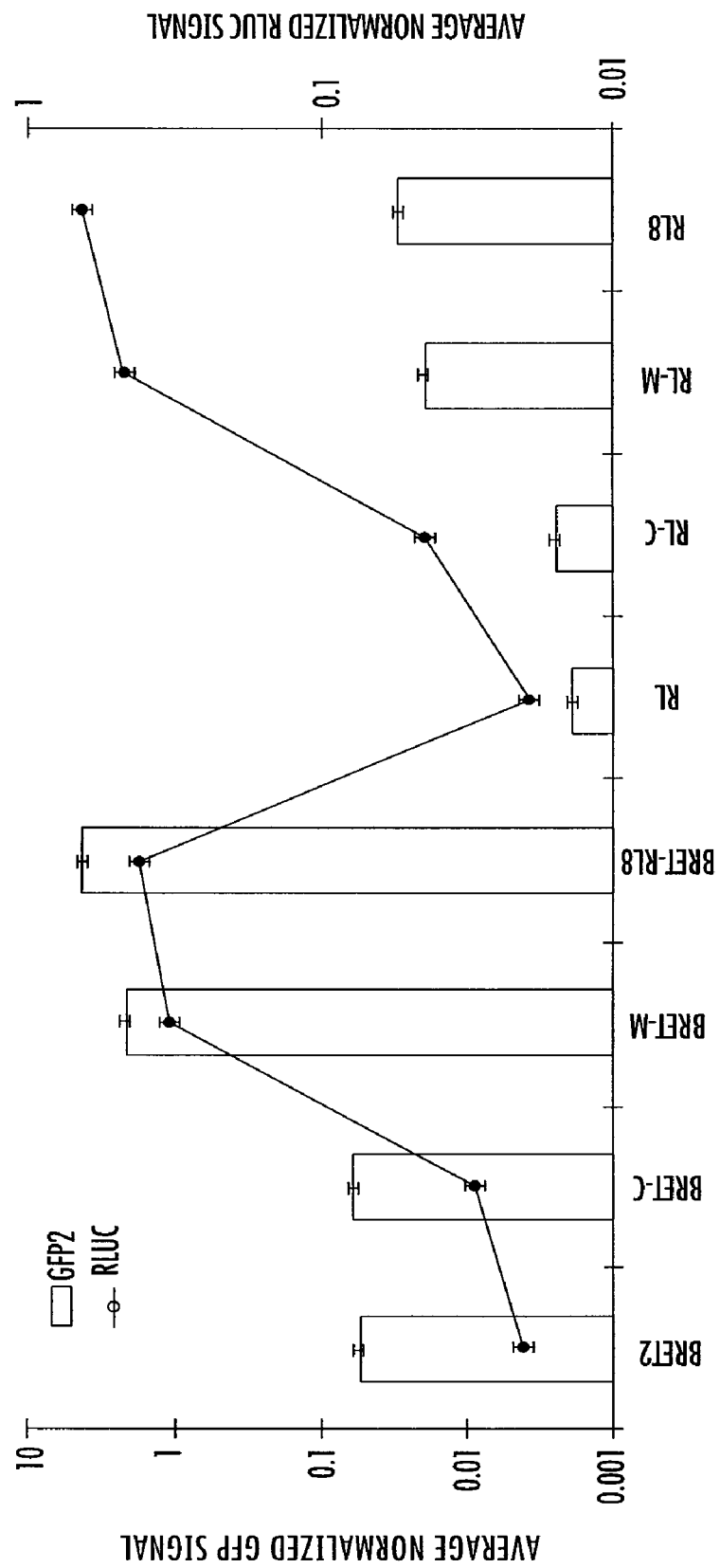
FIG. 7 illustrates a comparative chart showing normalized donor (RLUC) and acceptor (GFP2) signal as measured from 293T cells transiently transfected with the marked plasmid vectors. BRET2 represents GFP2-Rluc, BRET-C represents GFP2-Rluc C124A, BRET-M represents Rluc C124A/M185V, BRET-Rl8 represents GFP2-RLuc8, RL represents Rluc, RL-C represents RLuc C124A, RL-M represents RLuc C124A/M185V, and Rl8 represents Rluc8. CCD camera scans were performed by adding Coelenterazine400a to the well plates. The cells were co-transfected with CMV-FLuc plasmid and scaned at the same time using D-Luciferin substrate for normalization purposes.
Figure 8A:
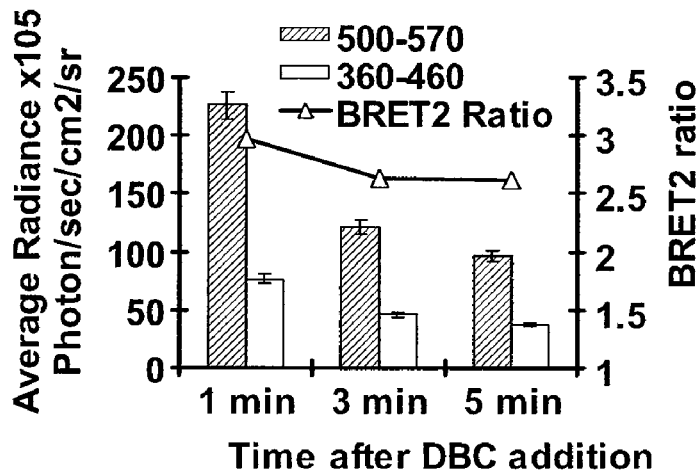
FIGS. 8A through 8D illustrate a semi-quantitative assessment of component BRET donor (Rluc) and acceptor (GFP2) proteins by western blotting (FIG. 8C) in selected clonal populations of HT1080 cells. BR2 represents GFP2-Rluc, Rl8 represents Rluc8, and Rl8-BR2 represents GFP2-Rluc8 plasmid constructs. α-tubulin monoclonal antibody was used as loading control.
Figure 8B:
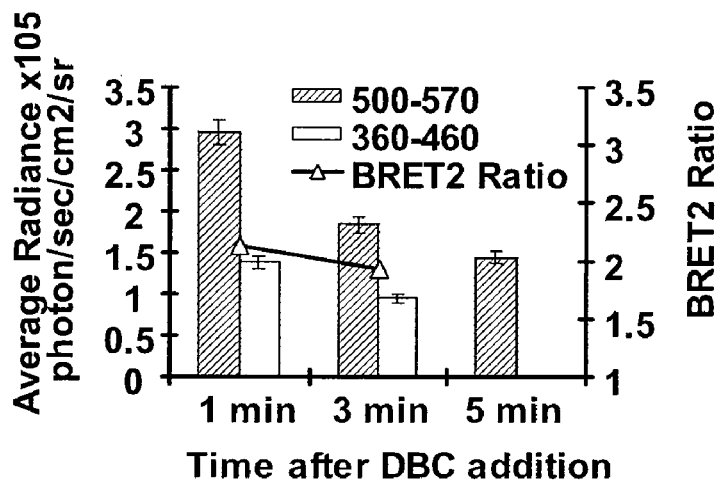
Figure 8C:

Results: In comparison to the cells expressing GFP$^2$-RLUC, normalized luciferase signal shows markedly significant (P<0.01) increase of 35 fold for GFP$^2$-RLUC8 fusion, and 25 fold for GFP$^2$-RLUCM185V, whereas the BRET signal shows 80 and 40 fold increases respectively. No significant improvements are noticed with the C124A mutation (FIG. 7). By establishing HT1080 cells constitutively over-expressing GFP$^2$-RLUC and GFP$^2$-RLUC8 with equal transgene expression, it was determined that each GFP$^2$-RLUC8 cell yields a BRET signal that is equivalent to approximately 30 GFP$^2$-RLUC expressing cells (FIGS. 8A, 8B and 8C). Further, the sensitivity of the new BRET vector was tested by imaging individual stable cells (FIGS. 9A and 9B) as well as cells at subcutaneous and deeper tissues of animals (FIGS. 10A and 10B).

Conclusion: These BRET vectors with improved BRET efficiency and sensitivity will likely accelerate the study of distance dependent processes such as protein-protein interaction and protein phosphorylation by measuring the events directly from live cells and from small animal models.

FIG. 7 illustrates a comparative chart showing normalized donor (RLUC) and acceptor (GFP2) signal as measured from 293T cells transiently transfected with the marked plasmid vectors. BRET2 represents GFP2-Rluc, BRET-C represents GFP2-Rluc C124A, BRET-M represents Rluc C124A/M185V, BRET-Rl8 represents GFP2-Rluc8, RL represents Rluc, RL-C represents RLuc C124A, RL-M represents RLuc C124A/M185V, and Rl8 represents Rluc8. CCD camera scans were performed by adding Coelenterazine400a to the well plates. The cells were co-transfected with CMV-FLuc plasmid and scaned at the same time using D-Luciferin substrate for normalization purposes.

FIGS. 8A and 8B illustrate comparative assessments on signal quantification from HT1080 cells stably over-expressing GFP2-Rluc8 (8A) and GFP2-Rluc (8B) plasmid vectors. Fixed numbers of cells (50000/well) were plated, and within 4 hours CCD camera imaging was performed by adding equal amount of Coelenterazine400a to the well plates. ROI values from corresponding wells were plotted (bars), as obtained from image data using either donor or acceptor filter. The line represents the calculated BRET ratios at each time point of measurements. Error bars represent SEM.

FIG. 8C illustrates a semi-quantitative assessment of component BRET donor (Rluc) and acceptor (GFP2) proteins by western blotting in selected clonal populations of HT1080 cells used for the above experiments. BR2 represents GFP2-Rluc, R18 represents Rluc8, and R18-BR2 represents GFP2-Rluc8 plasmid constructs. α-tubulin monoclonal antibody was used as loading control.

Figure 8D:
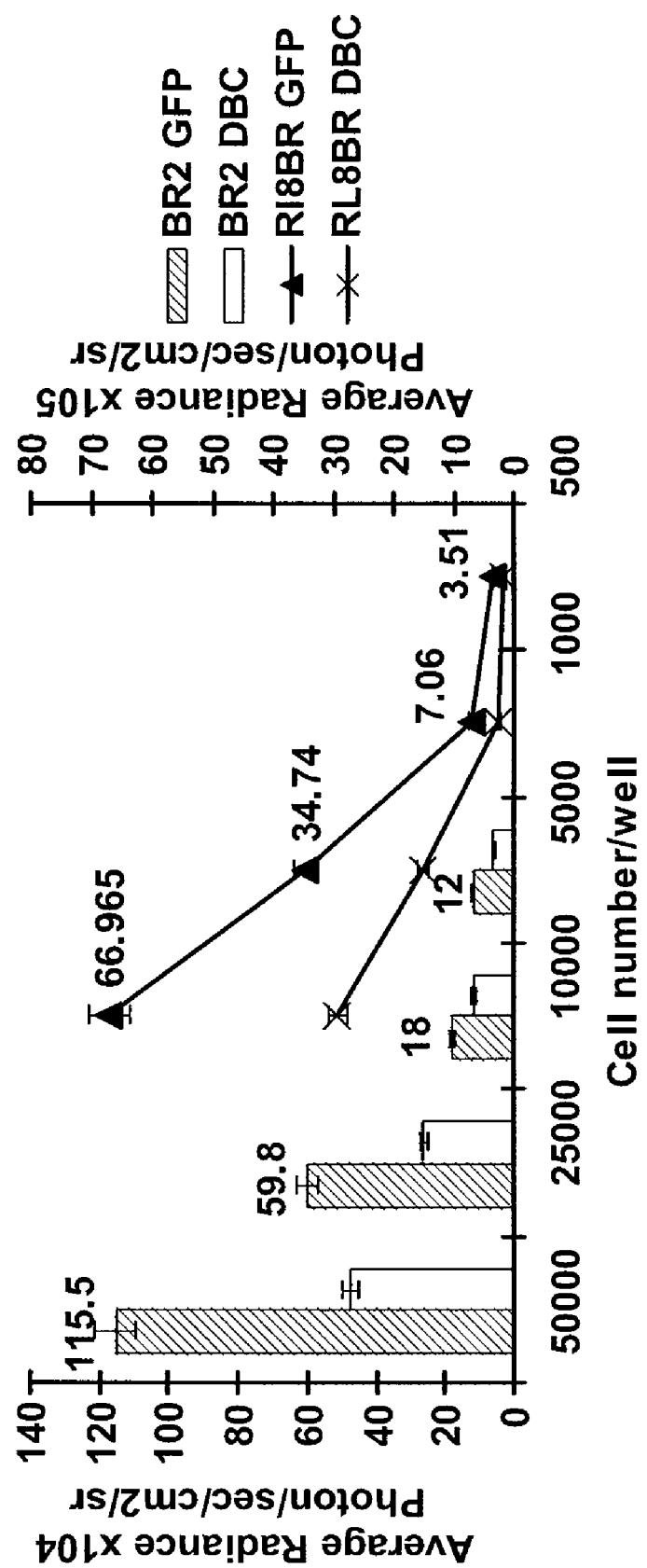

FIG. 8D illustrates that even though the two established cell lines (as in FIGS. 8A, B, and C) produce an equivalent amount of the fusion protein, fixed numbers of the GFP2-Rluc8 cells produce much higher photon than GFP2-Rluc cells.

Figure 9A:
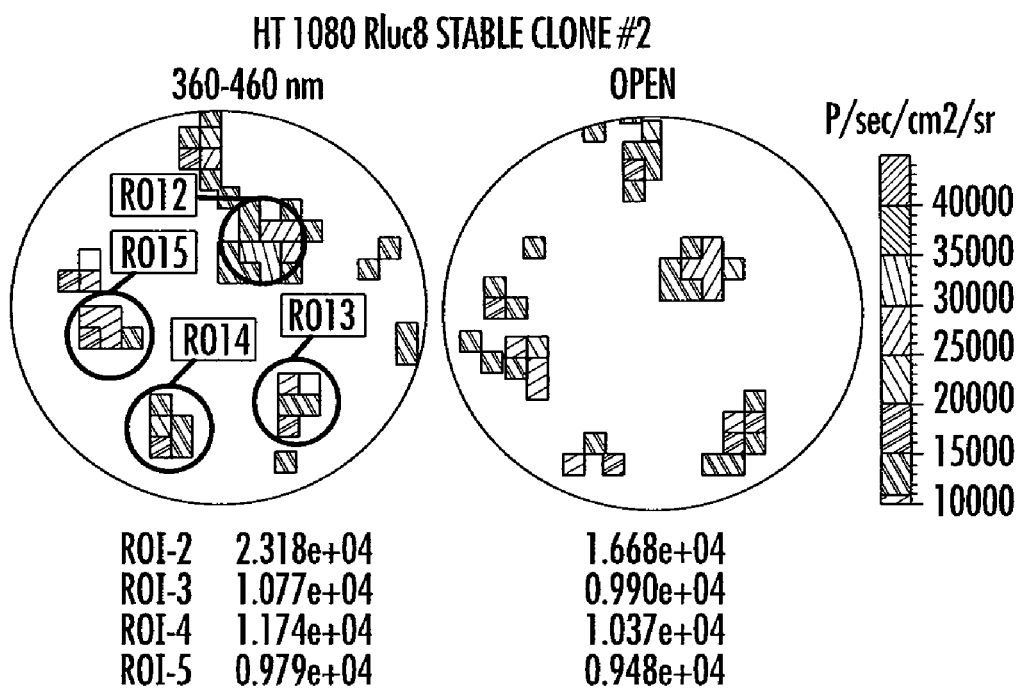
FIGS. 9A and 9B illustrate CCD camera images of HT1080 clonal cells stably over-expressing CMV-Rluc8 alone or CMV-GFP2-Rluc8 from individual wells of a 96 well plate. Cells were plated in isolation 4 hours before imaging. For cells expressing Rluc8 donor alone, luciferase enzyme, and Coelenterazine400a (DBC) substrate, reaction emission light is almost equivalent to the total light collected at open filter position. Whereas, on the cells expressing the Rluc8-GFP2 BRET pair, addition of the Coelenterazine400a substrate results in the emission of light that can be spectrally resolved using 500-570 nm and 360-460 nm filter attached CCD system. The photon values of the total emission light collected at open filter position confirms that the total light is equivalent to the sum of the photon values obtained by filter separation from various locations of the plate. Further, the ROI values also indicate that the photon values vary according to the number of cells at various positions of the plate.
Figure 9B:
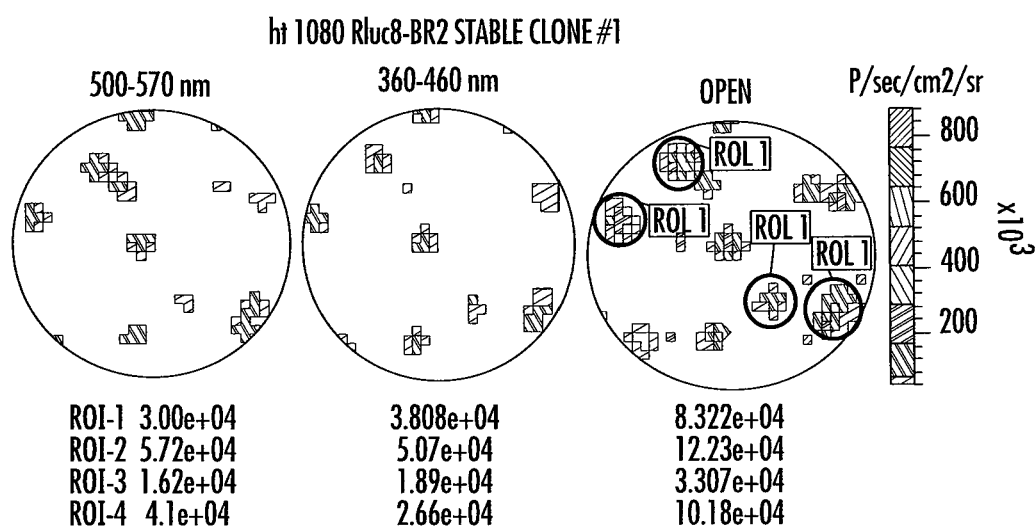
Figure 10A:
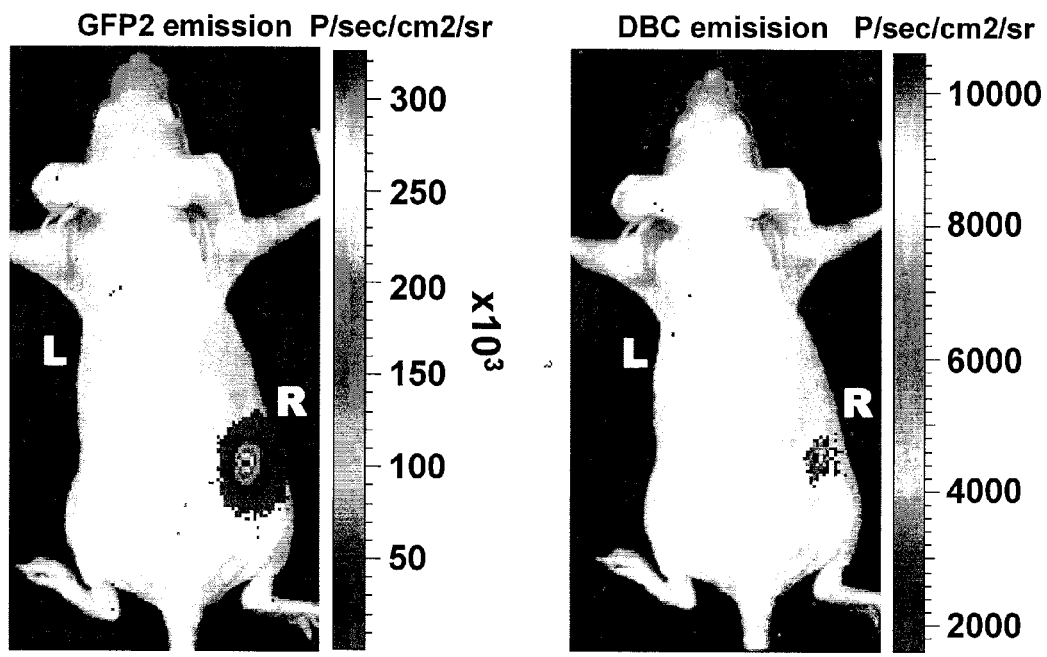
Figure 10B:
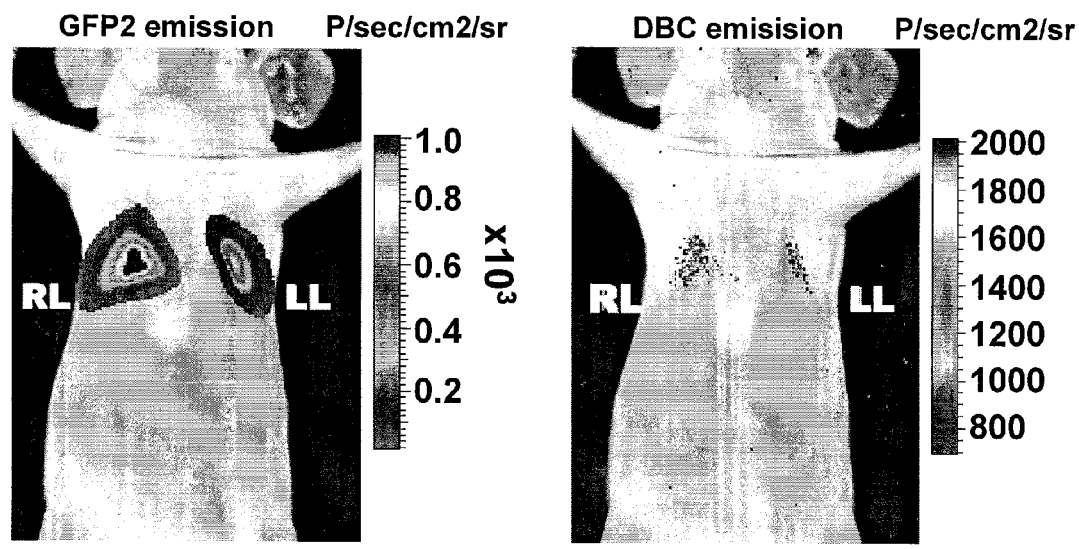

FIGS. 9A and 9B illustrate a CCD camera image of HT1080 clonal cells over-expressing CMV-Rluc8 alone (FIG. 9A) and HT1080 clonal cells over-expressing CMV-GFP2-Rluc8 (FIG. 9B) from individual wells of 96 well plate. It should be noted that the Rluc8 bleed-through signal on the GFP filter was below the detectable threshold. Signal detection from individual GFP2-Rluc clonal cells was not possible. For cells expressing Rluc8 donor alone, luciferase enzyme and Coelenterazine 400a (DBC) substrate reaction emission light is almost equivalent to the total light collected at open filter position. Whereas, on the cells expressing Rluc8-GFP2 BRET pair, addition of the Coelenterazine 400a substrate emits light that can be spectrally resolved using 500-570 nm and 360-460 nm filter attached CCD system. The photon values of the total emission light collected at open filter position confirms that the total light is equivalent to the sum of the photon values obtained by filter separation from various locations of the plate. Further, the ROI values also indicate that the photon values vary according to the number of cells at various positions of the plate.

FIGS. 10A and 10B illustrate the localization of BRET signal from subcutaneous and deep tissue structures of nude mouse implanted with constitutively over-expressing GFP2-Rluc8. In particular, FIG. 10A illustrates a CCD camera image of a representative mouse subcutaneously implanted with 500,000 GFP2-Rluc cells on the left shoulder (L) and the same number of GFP2-Rluc8 cells on the right flank (R). The mice were imaged by injecting 25 μg Coelenterazine400a intravenously using a 2 minutes image acquisition time. Therefore, using GFP2-Rluc8 BRET system events can be detected from a much lower number of cells located at subcutaneous tissue depth. This indicates that the improved sensitivity of the BRET vector will allow drug modulated protein-protein interactions from a tumor model at much earlier time points of tumor onset.

FIG. 10B illustrates a CCD camera image of a representative mouse implanted with 2 million GFP2-Rluc8 cells by intravenous injection. Thirty minutes after cell injection, the mice were imaged by injecting 75 μg Coelenterazine400a intravenously using a 3 minutes image acquisition time. For both FIGS. 10A and 10B, images were captured in sequence using the acceptor filter first followed by the donor filter, after a single dose of the mentioned Coelenterazine400a substrate amount. Therefore, using the GFP2-Rluc8 BRET system, both acceptor and donor signals can be measured from tissue depths such as lungs, and therefore the BRET ratio can be calculated as a measure of proximity of the interacting proteins.

Example 3

Luciferases, which have seen expansive employment as reporter genes in biological research, could also be used in applications where the protein itself is conjugated to ligands to create probes appropriate for use in small animal imaging. As the bioluminescence activity of commonly used Luciferases is too labile to permit this application, specific mutations of *Renilla* Luciferase, selected using a consensus sequence driven strategy, were screened for their serum stability and light output. Using this information, a total of 8 favorable mutations were combined to generate a mutant *Renilla* Luciferase (RLuc8) that exhibited a 150-fold improvement in murine serum stability, along with a 4-fold improvement in light output. Results of the mutational analysis were also used to generate a double mutant optimized for use as a reporter gene. The double mutant displayed twice the lability of the native enzyme while yielding a 5-fold improvement in light output. These variants of *Renilla* Luciferase, which exhibit significantly improved properties compared to the native enzyme, will allow enhanced sensitivity in existing Luciferase based assays.

Since the cloning of a Luciferase from the firefly in 1985, Luciferase genes have become essential components of biological research. They are used ubiquitously as reporter genes in cell culture experiments, and their use as reporters has been extended into the context of small animal imaging.

The advantage of using a bioluminescent entity to label a protein over similar fluorescent or radioactive approaches, is that in the context of small animal imaging the bioluminescent approach has the potential to be more sensitive.

Luciferases that use coelenterazine as their substrate are more appropriate for application as bioluminescent tags, as these enzymes are not ATP dependent and in general require only molecular oxygen in addition to coelenterazine for luminescence. From this group of proteins, the Luciferase from *Renilla reniformis* (RLuc) is the best characterized in addition to being of a size (36 kDa) more appropriate for use as a tag.

In this example, mutations that could alter RLuc's stability have been identified. In addition, mutations that increased the light output of RLuc, particularly when used with analogs of coelenterazine, have been identified. By combining these mutations appropriately, a mutant RLuc was generated with enhanced stability and light output that is optimized for use as a bioluminescent tag, as well as a mutant RLuc with enhanced lability and light output for use as a reporter gene.

Results

Computational Predictions for *Renilla* Luciferase: Via sequence similarity searches, RLuc was predicted to contain a characteristic α/β-hydrolase fold from around amino acid 71 to 301, and was found to have a high level of homology (34-56% similar) to a number of bacterial haloalkane dehalogenases. FIGS. 13A through 13C show the alignment of RLuc with the most similar of the haloalkane dehalogenases.

Mutagenesis of *Renilla* Luciferase and Screening: In the hopes of further enhancing the stability of RLuc beyond that achieved with the C124A mutation (C152A), a number of further mutations were explored. Candidate mutations were chosen from the alignment data at positions where RLuc most clearly diverged from the consensus sequence. For instance, the candidate mutation A55T was chosen because RLuc harbors the aliphatic amino acid alanine at position 55, while all of the dehalogenases harbor a hydroxylic residue of either threonine or serine. Similarly, S287L was chosen as a candidate because RLuc contains a hydroxylic residue at this position, differing from the consensus aliphatic residue. The M253L mutation substitutes an aliphatic residue for another aliphatic, but brings the RLuc sequence into consensus with the highly conserved local sequence near this position.

Complete results with respect to serum stability, activity, and emission spectra peaks are summarized in Table 1 for 25 initial mutations, on a background of RLuc with the C124A mutation, along with data from several other constructs described below. Note that activity was defined as a 10 s integration of the light output curve in order to disfavor mutations that merely increased the burst value at the expense of total light output. Representative serum stability data and emission spectra are shown in FIGS. 14A and 14B and, respectively.

TABLE 1

Mutations of RLuc altered serum stability and light output. Activity values are the result of integrating over 10 s and are not peak burst values. "Native" indicates the native substrate, while "bc", "cp", "n", and "bdc" indicate the analogs benzyl-coelenterazine, coelenterazine-cp, coelenterazine-n, and bisdeoxycoelenterazine, respectively (Chemical ctructures are shown in FIG. 11). The results for the native enzyme are reported in absolute units, while the values for the mutants are reported as relative to the native enzyme for the given substrate. Bisdeoxycoelenterazine's emission spectrum is significantly blue shifted from the other substrates, and since the luminometer's enhanced spectral sensitivity at these shorter wavelengths was not corrected for, the absolute unit values represent an overestimation of the real values. The wavelength measurements shown are for native coelenterazine, and the mean and peak wavelengths differ due to the non-symmetrical distribution of the emission spectrum. C124A-ΔMyc differs from C124A in that the Myc epitope introduced by the bacterial expression plasmid has been removed in order to make it directly comparable to RLuc8. RLuc8 contains the mutations A55T, C124A, S130A, K136R, A143M, M185V, M253L, and S287L. In cases were a particular protein was produced, purified, and assayed independently three or more times, the standard error of the mean is reported.

Table 1 of Example 3

| | Activity (photons/s/mole enzyme) | | | | | Serum $\tau_{1/2}$ (h) | | Wavelength (nm) | |
|---|---|---|---|---|---|---|---|---|---|
| | native | bc | cp | n | bdc | mouse | rat | peak | mean |
| Native RLuc | $(3.2 \pm 0.3) \times 10^{22}$ | $5.4 \times 10^{22}$ | $1.7 \times 10^{22}$ | $8.3 \times 10^{21}$ | $5.8 \times 10^{19}$ | 0.9 | 0.4 | 482 | 497 |
| Initial Mutations | Activity (relative to RLuc) | | | | | | | | |
| C124A | 1.2 ± 0.1 | 0.75 | 0.79 | 0.63 | 0.68 | 7.1 ± 0.4 | 6.6 ± 0.5 | 482 | 498 |
| C124A-ΔMyc | 1.3 ± 0.1 | 0.91 | 1.1 | 0.87 | 1.0 | 4.0 | 4.5 | 481 | 499 |
| F33R/I34M/C124A | 0.15 | 0.15 | 0.16 | 0.12 | 0.20 | 0.3 | 0.3 | 481 | 497 |
| E44G/C124A | 0.94 | 0.78 | 0.74 | 0.66 | 0.98 | 2.6 | 3.3 | 486 | 502 |
| A54G/A55G/C124A | 0.12 | 0.10 | 0.06 | 0.15 | 0.19 | 2.4 | 3.0 | 476 | 492 |
| A54P/A55T/C124A | 0.21 | 0.15 | 0.11 | 0.38 | 0.22 | 119 | 129 | 470 | 483 |
| A54P/C124A | 0.05 | 0.04 | 0.05 | 0.08 | 0.06 | 14 | 13 | 468 | 482 |
| A55T/C124A | 1.7 | 1.2 | 0.58 | 1.4 | 2.4 | 30 | 29 | 486 | 504 |
| F116L/C124A | 1.3 | 1.0 | 1.3 | 0.88 | 1.8 | 11 | 9.4 | 486 | 502 |
| C124A/S130A | 1.7 | 1.4 | 1.7 | 1.4 | 2.6 | 18 | 14 | 482 | 498 |
| C124A/K136R | 2.5 ± 0.3 | 2.1 | 1.9 | 1.9 | 2.6 | 12 | 11 | 482 | 498 |
| C124A/A143M | 1.7 | 1.3 | 0.95 | 1.5 | 1.6 | 30 | 29 | 480 | 497 |
| C124A/F180A | 0.02 | 0.01 | 0.03 | 0.01 | 0.01 | 1.6 | 1.6 | 488 | 504 |
| C124A/M185V | 3.4 | 3.0 | 15 | 7.8 | 44 | 5.7 | 3.7 | 485 | 500 |
| C124A/M191L | 1.1 | 0.99 | 0.97 | 1.0 | 1.2 | 6.5 | 5.1 | 480 | 496 |
| C124A/E195S/P196D | 0.12 | 0.10 | 0.12 | 0.10 | 0.15 | 1.0 | 0.7 | 482 | 498 |
| C124A/F199M | 0.58 | 0.44 | 0.53 | 0.49 | 0.46 | 6.7 | 6.0 | 480 | 495 |
| C124A/L203R | 0.55 | 0.55 | 0.52 | 0.41 | 0.43 | 2.7 | 2.2 | 484 | 501 |
| C124A/G229E | 0.02 | 0.01 | 0.03 | 0.03 | 0.01 | 1.9 | 1.8 | 473 | 490 |
| C124A/Q235A | 1.2 | 1.1 | 1.1 | 1.0 | 1.2 | 3.3 | 3.6 | 473 | 489 |

TABLE 1-continued

Mutations of RLuc altered serum stability and light output. Activity values are the result of integrating over 10 s and are not peak burst values. "Native" indicates the native substrate, while "bc", "cp", "n", and "bdc" indicate the analogs benzyl-coelenterazine, coelenterazine-cp, coelenterazine-n, and bisdeoxycoelenterazine, respectively (Chemical ctructures are shown in FIG. 11). The results for the native enzyme are reported in absolute units, while the values for the mutants are reported as relative to the native enzyme for the given substrate. Bisdeoxycoelenterazine's emission spectrum is significantly blue shifted from the other substrates, and since the luminometer's enhanced spectral sensitivity at these shorter wavelengths was not corrected for, the absolute unit values represent an overestimation of the real values. The wavelength measurements shown are for native coelenterazine, and the mean and peak wavelengths differ due to the non-symmetrical distribution of the emission spectrum. C124A-ΔMyc differs from C124A in that the Myc epitope introduced by the bacterial expression plasmid has been removed in order to make it directly comparable to RLuc8. RLuc8 contains the mutations A55T, C124A, S130A, K136R, A143M, M185V, M253L, and S287L.
In cases were a particular protein was produced, purified, and assayed independently three or more times, the standard error of the mean is reported.
Table 1 of Example 3

|  | Activity (photons/s/mole enzyme) | | | | | Serum $\tau_{1/2}$ (h) | | Wavelength (nm) | |
| --- | --- | --- | --- | --- | --- | --- | --- | --- | --- |
|  | native | bc | cp | n | bdc | mouse | rat | peak | mean |
| C124A/M253L | 1.9 | 1.4 | 1.6 | 1.6 | 1.7 | 15 | 10 | 471 | 488 |
| C124A/S257G | 1.1 | 0.95 | 1.3 | 1.1 | 3.0 | 1.3 | 1.4 | 477 | 493 |
| C124A/F261L/F262L | 0.00 | 0.00 | 0.00 | 0.00 | 0.00 | N/D | | N/D | |
| C124A/F262L | 0.03 | 0.03 | 0.01 | 0.06 | 0.03 | 5.8 | 6.4 | 478 | 495 |
| C124A/S287L | 3.9 | 2.8 | 3.4 | 5.0 | 9.5 | 28 | 20 | 478 | 496 |
| C124A/M295I | 1.0 | 0.83 | 0.57 | 0.72 | 0.86 | 5.0 | 4.9 | 480 | 497 |
| C124A/K300A | 1.1 | 1.0 | 1.1 | 1.0 | 1.3 | 3.5 | 3.9 | 481 | 497 |
| Stabilized Luciferase | | | | | | | | | |
| RLuc8 | 4.3 ± 0.2 | 3.0 | 5.8 | 8.8 | 59 | 253 ± 58 | 88 ± 12.4 | 487 | 503 |
| Active Site Mutations | | | | | | | | | |
| RLuc8/D120A | 0.000 | 0.001 | 0.001 | 0.003 | 0.21 | >100 | >100 | N/D | |
| RLuc8/D120N | 0.023 | 0.016 | 0.050 | 0.34 | 5.1 | >100 | >100 | N/D | |
| RLuc8/E144A | 0.000 | 0.000 | 0.000 | 0.000 | 0.000 | 57 | 13 | N/D | |
| RLuc8/E144Q | 0.000 | 0.000 | 0.000 | 0.000 | 0.002 | >100 | >100 | N/D | |
| RLuc8/H285A | 0.023 | 0.020 | 0.046 | 0.028 | 0.20 | >100 | 21 | N/D | |
| Destabilized Luciferases | | | | | | | | | |
| M185V | 4.4 | 2.6 | 12 | 4.1 | 20 | 0.8 | 0.3 | N/D | |
| M185V/Q235A | 4.8 | 2.7 | 14 | 7.1 | 20 | 0.5 | 0.2 | N/D | |

N/D—Not Determined.

The assayed values for RLuc reported in Table 1 corresponded well with previous values reported in the literature. In terms of stability under serum like conditions, our reported values for recombinant RLuc ($\tau_{1/2}$=0.4–0.9 h) are in line with others who reported a half-life of 0.6 h for recombinant RLuc in hamster blood at 37° C., as well as another who reported a half-life of 0.5 h for recombinant RLuc in a high ionic strength buffer. The measured emission peak for RLuc with coelenterazine (482 nm) corresponded exactly with a previously published value of 482 nm for RLuc purified directly from *Renilla reniformis*. Peak light flux from recombinant RLuc was determined to be $1.2\pm0.2\times10^{23}$ photons/s/mole enzyme when in the presence of 24 μM coelenterazine. This value corresponds acceptably with the value of $6.5\times10^{22}$ photons/s/mole enzyme reported for RLuc purified directly from *Renilla reniformis*, and $9\times10^{22}$ photons/s/mole enzyme reported for recombinant RLuc.

Combining Mutations for a Stabilized Luciferase: For the purpose of generating a mutant RLuc appropriate for use as a bioluminescent tag in small animal imaging applications, the initial mutations were judged for serum stability and light output. In all, 7 mutations were deemed as having the most favorable properties and were combined, along with the C124A mutation, into a single protein designated as "RLuc8" (SEQ ID NO: 2). The 8 mutations present in RLuc8 are A55T, C124A, S130A, K136R, A143M, M185V, M253L, and S287L. Since the Myc epitope was removed during the cloning of RLuc8, a C124A mutant was constructed without the Myc epitope to facilitate a valid comparison (C124A-Dmyc).

The stability, activity, and spectra peak values for these two enzymes are shown in Table 1. When compared to the native enzyme, RLuc8 exhibited a greater than 4 fold increase in activity, a 150 fold increase in serum stability, and a 5 nm red shift in the emission spectrum. Compared to the C124A mutant, RLuc8 showed a 3 fold increase in activity and at least a 20 fold improvement in murine serum stability.

Light scattering results suggest RLuc8 exists as a monomer in solution, as molar mass moment calculations based on the multiangle scattering indicate a molecular weight of 33.8 kDa (error: 7%) with a relatively low polydispersity across the gel filtration elution profile (~11%).

Quantum Yield and Kinetic Parameters of Mutants: To understand the basis for RLuc8's higher activity, both quantum yield and kinetic measurements were undertaken. The results shown in Table 2 indicate that RLuc8 had a 30% improvement in quantum yield for native coelenterazine, and about a 30 fold increase in quantum yield for bisdeoxycoelenterazine. A Michaelis-Menten model was fit to initial reaction velocity data for coelenterazine concentrations in the range of 0.038 to 24 μM. The results for RLuc, the C124A mutant, and RLuc8 were $K_m$=2.9±1.0, 2.7±0.8, 1.6±0.2 μM, and $k_{cat}$=3.9±0.4, 4.7±0.4, 4.9±0.1 $s^{-2}$, respectively, with the errors presented representing the formal standard errors of the fitted parameters. The results for RLuc are roughly consistent with a previously published $K_m$ value of 2 μM for RLuc in the presence of benzyl-coelenterazine.

TABLE 2

Mutations of RLuc altered quantum yield. Standard errors of the mean are reported.
Table 2 of Example 3

| | Quantum Yield (%) | | | | |
|---|---|---|---|---|---|
| | native | bc | cp | n | bdc |
| Native RLuc | 5.3 ± 0.1 | 3.2 ± 0.04 | 4.7 ± 0.03 | 6.1 ± 0.2 | $(6.1 ± 0.9) \times 10^{-3}$ |
| C124A | 5.4 ± 0.3 | 3.6 ± 0.1 | 5.2 ± 0.1 | 6.4 ± 0.01 | $(7.7 ± 0.5) \times 10^{-3}$ |
| A55T/C124A | 5.7 ± 0.2 | 3.9 ± 0.1 | 4.5 ± 0.1 | 5.7 ± 0.1 | $(1.0 ± 0.9) \times 10^{-3}$ |
| C124A/S130A | 5.3 ± 0.1 | 3.4 ± 0.04 | 5.0 ± 0.1 | 5.9 ± 0.2 | $(6.7 ± 0.3) \times 10^{-3}$ |
| C124A/K136R | 5.4 ± 0.1 | 3.3 ± 0.1 | 5.1 ± 0.1 | 6.0 ± 0.1 | $(7.1 ± 0.3) \times 10^{-3}$ |
| C124A/A143M | 5.2 ± 0.3 | 3.5 ± 0.1 | 4.8 ± 0.1 | 5.8 ± 0.2 | $(6.3 ± 0.7) \times 10^{-3}$ |
| C124A/M185V | 6.9 ± 0.3 | 6.3 ± 0.1 | 10.1 ± 0.2 | 9.4 ± 0.4 | $(174.4 ± 6.7) \times 10^{-3}$ |
| C124A/M253L | 5.5 ± 0.1 | 3.5 ± 0.1 | 5.1 ± 0.2 | 5.8 ± 0.1 | $(7.6 ± 0.3) \times 10^{-3}$ |
| C124A/S287L | 6.1 ± 0.2 | 5.0 ± 0.1 | 7.2 ± 0.3 | 7.7 ± 0.2 | $(20.9 ± 0.6) \times 10^{-3}$ |
| RLuc8 | 6.9 ± 0.1 | 6.1 ± 0.1 | 8.9 ± 0.1 | 9.6 ± 0.4 | $(198.2 ± 8.5) \times 10^{-3}$ |

Mutations to Test Proposed Active Site: Based on the residues known to be critical for haloalkane dehalogenases activity, D120, E144, and H285 were believed to be important for Renilla Luciferase activity as well. The locations of these residues in a homology model of Renilla Luciferase are shown in FIG. 13B. To test the hypothesis that these residues include a portion of the enzyme's active site, further mutations were made at these sites on the RLuc8 construct, with the results shown in Table 1. With respect to maintaining luciferase activity, mutations at these proposed active site residues were deleterious.

Combining Mutants for a Destabilized Luciferase: In order to construct brighter yet destabilized mutants, the initial double mutants where compared to the single mutant C124A to identify mutations that led to increased activity without increasing serum stability (e.g., M185V) or decreased serum stability without affecting activity (e.g., Q235A, S257G). Combining these mutations in the absence of C124A resulted in the mutants M185V and M185V/Q235A (Table 1) that showed increased lability and activity in comparison to RLuc.

Testing of Mutants in Mammalian Expression: In order to determine whether the in vitro data gathered for the RLuc mutants and RLuc8 would translate into the context of a mammalian reporter gene, expression vectors were constructed for RLuc, C124A, C124A/M185V, and RLuc8 in a pcDNA 3.1 backbone. These mammalian expression plasmids were then transiently transfected into 293T or CHO cells. The results 24 hours post transfection, shown in Table 3, demonstrated increased light output for the mutants consistent with the in vitro data.

TABLE 3

Transient transfection of native RLuc and several mutants into 293T or CHO cells. The Luciferases for this study were in pcDNA 3.1 plasmids under the control of the constitutive promoter from cytomegalovirus (CMV). Samples were done in triplicate, data is in units of photons × $10^6$/s/cm$^2$/steradian, and the reported error is the standard error of the mean. For a given cell line, all differences between groups were significant at p ≦ 0.06 using a two-tailed t-test with the incorporation of a Bonferroni-Holms correction for multiple comparisons.
Table 3 of Example 3

| | 293T | CHO |
|---|---|---|
| RLuc | 22.5 ± 0.7 | 11.7 ± 1.2 |
| C124A | 62.8 ± 12.9 | 64.0 ± 4.9 |
| C124A/M185V | 174.1 ± 25.7 | 172.4 ± 8.4 |
| RLuc8 | 328.8 ± 34.5 | 281.8 ± 42.1 |

Discussion

The amino acid sequence of Renilla reniformis Luciferase, along with that of the closely related Renilla mülleri Luciferase, contains a characteristic α/β-hydrolase fold sequence. This fold pattern is found in enzymes that catalyze a diverse range of chemical reactions in all kingdoms of life. Interestingly, within the α/β-hydrolase family, RLuc shows the highest level of similarity to the bacterial haloalkane dehalogenases, enzymes that catalyze the hydrolytic detoxification of halogenated compounds. This similarity even extends to the conserved haloalkane dehalogenase catalytic triad, present as D120, E144, and H285 in Rluc. The level of similarity is unexpected as RLuc is an oxygenase and Renilla reniformis is not a bacterium.

The evolution of a coelenterazine using oxygenase from an enzyme that catalyzes an unrelated reaction would not, in fact, present a great challenge for evolution. Coelenterazine chemiluminesces easily in aprotic solutions, and an initial enzyme would have to provide little more than a hydrophobic environment for coelenterazine to achieve some low level of bioluminescence. The high level of primary sequence similarity between RLuc and the bacterial haloalkane dehalogenases, however, is harder to explain, and it may indicate that the ancestral Luciferase gene was originally contained in a bacteria species and passed into the evolutionary predecessor of the bioluminescent Renilla species in a horizontal gene transfer event.

Researchers have reported results from sequentially mutating the three cysteines to alanine in a version of Renilla Luciferase engineered for mammalian cell secretion. Their hypothesis was that, in this secreted version of Renilla, these cysteines would have a propensity to form inactivating disulfide bonds in the oxidizing environment of the protein secretion pathway. They reported a complete loss of activity when mutating out the second cysteine residue (C73), which can now be explained in light of alignment data showing a conserved cysteine near this location across all but one of the bacterial haloalkane dehalogenases examined. They also reported enhanced stability of the enzyme when the third cysteine (C124) was replaced, and suggested that this was due to the blocking of unintended disulfide bond formation in non-reducing environments. The homology model, however, indicates that the third cysteine is buried, and removal of a potential disulfide bond formation is unlikely to explain the increased stability seen for this mutant after protein folding. More likely, the C124A mutation increases stability by resulting in better packing of the hydrophobic core. Interestingly, the alignment data shows that the bacterial haloalkane dehalogenases favor an alanine at this position.

The interpretation of the results in light of the protein alignment data led to the examination of a mutation strategy where candidate mutations would be picked at locations where RLuc clearly diverged from the bacterial consensus. This strategy was initially predicated upon the hypothesis that, following a horizontal gene transfer event, mutations would accumulate in the ancestral RLuc gene that are either neutral only in the specific context of the *Renilla* lumisomes, or required for the association with and resonance energy transfer to the green fluorescent protein (GFP) homo-dimer that is the normal light emitter in *Renilla*.

The reason a consensus guided approach works efficiently may simply be, that the chosen candidate mutations are more likely to be tolerated within the folded protein than if the mutations had been selected at random.

Enhanced protein packing is an oft-cited reason for stability inducing effects, and it is possibly the mechanism through which many of the present mutations increase the protein's resistance to inactivation in the serum environment. Some of these stability conferring mutation sites may also have been important in the aforementioned in vivo interaction between RLuc and *Renilla* GFP. Now in the environment of in vitro assays absent of GFP, the wild type amino acids may instead be detrimental.

Three of the mutations, K136R, M185V, and S287L, showed sizable increases in the light output of the enzyme. In the case of M185V, a portion of the increase in light output can be explained by enhanced quantum yield, especially for the coelenterazine analogs, with the difference assumed to arise from enhanced kinetics. The disproportionate increase in light output seen with M185V for several of the coelenterazine analogs leads to the possibility that the light increase and specificity decrease are related, and that M185 may be positively selected for in RLuc and *Renilla mülleri* Luciferase to insure specificity of the reaction. This trade off between substrate recognition and light output could arise if the 185 position was important in substrate recognition. The alignment data gives some credence to this hypothesis, as M185 is located in the "cap", a domain often used for substrate specificity in the haloalkane dehalogenases. The location of M185 in the homology model lends further support, as its placement atop the presumptive catalytic site (formed by D120, E144, and H285) would be an appropriate position for conferring substrate specificity to the Luciferase. While not wishing to be bound by theory and while the interpretations in this example are based on a homology derived protein structure, preliminary crystallographic data confirms these interpretations (unpublished).

S287L, while not located in the active site, is close enough to the active site residue H285 that slight alterations in the structure of the enzymatic pocket induced by S287L could explain the slight increase in quantum yield and the larger increase in light output seen with this mutation.

K136, on the other hand, is located on the surface of the protein approximately 20 Å distant from the presumptive active site. It is still possible that the increased light output seen with the K136R mutation could arise through long range perturbations in the folding of the active site, especially as K136 lies in a loop between the active site residues D120 and E144. Incidentally, *Renilla mülleri* Luciferase contains an arginine at this position.

Although not intending to be bound by theory, an alternative possibility for the increases in light output, especially for M185 and S287, is that these residues are involved in the transfer of energy to the GFP homo-dimer that interacts with RLuc in nature. As such, these residues have been selected for their ability to transfer energy to the GFP fluorophore and not for their ability to optimize the quantum yield of the Luciferase on its own.

Using the above-described assay, RLuc8 displayed an about 4 fold increase in light output versus RLuc. For RLuc8, combining the increases in quantum efficiency with the enhanced Michaelis-Menten parameters would only predict an about 70% increase in light output over RLuc. Additionally, the Michaelis-Menten model could not satisfactorily fit the reaction progress curves, nor the initial reaction velocity at the highest coelenterazine concentration tested (118 µM), even when product inhibition was incorporated into the model. Previous attempts at elucidating a satisfactory kinetic model for RLuc have failed.

Transient transfection of C124A, C124A/M185V, and RLuc8 into mammalian cells demonstrated that the basic trends derived from the in vitro mutation analysis are applicable in the context of a mammalian cell as well. Since C124A and C124A/M185V exhibited approximately the same in vitro serum stability, the approximately 3 fold increase in light for C124A/M185V relative to C124A may arise directly from the ~3 fold increase in activity seen in vitro. The increased light output for RLuc8 in the mammalian transfection study may arise from a combination of its increased in vitro stability and activity.

Luciferases are extraordinarily useful in a variety of experiments that require reporter genes. In instances where the reporter gene is constitutively expressed (e.g., cell trafficking studies), RLuc8 should be advantageous because of its greatly increased light output compared to RLuc in mammalian cells.

In many reporter gene experiments, however, the investigator wishes to follow the dynamics of gene induction and suppression. In these contexts, the high stability of RLuc8 could be a detriment to the experiment, as the stability of this protein would obscure the monitoring of transient gene expression changes. The single mutant M185V and the double mutant M185V/Q235A could be of great utility in these cases, as both these mutants show an about 4 fold increase in activity as well as an increase in protein lability relative to RLuc.

An issue with the use of coelenterazine catalyzing Luciferases for reporter gene assays in mammalian cells is that coelenterazine is a substrate for MDR1 P-glycoprotein (Pgp). While the resultant transport of coelenterazine out of mammalian cells can be used to measure levels of Pgp, in most studies this phenomenon leads to an inadvertent modulation of signal intensity. For this reason, there has been interest in the coelenterazine analogs coelenterazine-cp and coelenterazine-n, as they are not substrates for Pgp. These analogs, however, suffer from reduced light output when used with RLuc (see Table 1) as well as higher background rates of auto-chemiluminescence. The M185V mutation greatly reduces the disadvantages of these alternative substrates. In the case of coelenterazine-cp, the signal to background ratio when using the M185V mutation should be nearly equivalent whether the native substrate or the analog is used. RLuc8 is not as effective at using coelenterazine-cp as the M185V mutation alone, most likely because the A55T mutation present in RLuc8 decreases its ability to use this substrate.

Bisdeoxycoelenterazine (Coelenterazine 400a or DBC) has been proposed as a better analog to use with bioluminescence resonance energy transfer (BRET) studies because of the increased separation between the bioluminescence and the fluorescence spectrums. Bisdeoxycoelenterazine, however, suffers from low light output when used with native RLuc (Table 1) because of poor quantum yield (Table 2). Although low bioluminescence quantum efficiency doesn't necessarily imply low light output from BRET, and increased bioluminescence quantum efficiency may not translate into a corresponding increase in BRET output, preliminary data indicate that bioluminescence quantum yield and BRET output are indeed related, at least when the acceptor moiety is a variant of *Aequorea* GFP. Both RLuc8 and the M185V mutation may be of great utility in these BRET assays, as they confer about a 20-60 fold increase in light output with bis-deoxycoelenterazine. Interestingly, although C124A alone doesn't significantly improve utilization of bisdeoxycoelenterazine, it appears to facilitate the M185V mutation, as C124A/M185V has about a 2 fold better light output with this substrate compared to M185V alone.

In summary, mutants of RLuc have been characterized with respect to serum stability and light output, and these results have been used to develop Luciferases optimized for different purposes. An 8 mutation form of RLuc (RLuc8) (SEQ ID NO: 3) was created that has greatly improved characteristics for use as a bioluminescent label. Compared to the native enzyme, RLuc8 exhibited a 150 fold stability improvement in murine serum, a 4 fold improvement in light output, and a 5 nm red shift in the emission spectrum. The enhancement in light output arises from a combination of increases in quantum yield and improved kinetics. A double mutant of RLuc (M185V/Q235A) was created that has improved performance as a reporter gene. Compared to the native enzyme it has half the stability, as measured in murine serum, while incorporating a close to 5 fold improvement in light output. These optimized *Renilla* Luciferases represent significant improvements that increase the sensitivity of Luciferase based assays for both in vitro experiments and in vivo imaging.

Methods and Materials

Materials: Coelenterazine was from Prolume (Pinetop, Ariz.). Benzyl-coelenterazine (coelenterazine-h) was obtained from Dr. Bruce Bryan. Coelenterazine-n and coelenterazine-cp were from Biotium (Hayward, Calif.). Bis-deoxycoelenterazine (coelenterazine-400a, di-dehydro coelenterazine, DeepBlueC) was from Perkin Elmer (Boston, Mass.). The chemical structures of these compounds are shown in FIG. 11. Coelenterazine and the analogs were dissolved in propylene glycol and stored in small aliquots at −80° C.

Luminometer Calibration: Light measurements were made using a Turner 20/20 and later a Turner 20/20n luminometer (Turner Designs, Sunnyvale, Calif.). The luminometers were calibrated to absolute units (photons/s) using the luminol light standard performed in dimethyl sulfoxide (DMSO). No corrections were applied for the spectral sensitivity of the luminometer, as the spectral peak of luminol chemiluminescence in DMSO (486 nm) is close to the spectral peak of *Renilla* Luciferase bioluminescence (482 nm).

Computational Prediction: A PSI-BLAST search, performed using the PredictProtein server, identified a number of sequences homologous to RLuc. An alignment between RLuc and the 9 most similar sequences (46% similarity) was then generated using CLUSTAL W.

A homology model of RLuc was built with SWISS-MODEL (v3.5) using the default parameters. In generating this homology model, SWISS-MODEL utilized several crystal structures of the haloalkane dehalogenase LinB from *Sphingomonas paucimobilis* (PDB files 1iz8, 1k63, 1k6e, 1iz7, and 1mj5).

Construction of *Renilla* Luciferase Mutants: The hrluc gene from the plasmid phRL-CMV (Promega, Madison, Wis.) was used as the initial template for cloning. This gene is a human codon useage optimized version of rluc, and encodes a protein identical to RLuc with the exception of a T2A substitution. To construct a bacterial expression plasmid, PCR was used to remove the stop codon and to replace the N-terminal methionine codon with a pelB leader sequence. The pelB leader sequence, consisting of the first 22 codons of the pectate lyase B gene from *Erwinia carotovora*, directs protein expression into the bacterial periplasm and is cleaved from the final protein product. Using NcoI and HindIII restriction sites, the PCR product was inserted into the pBAD/Myc-His A plasmid (Invitrogen, Carlsbad, Calif.), which adds a Myc epitope, a 6×His tag, and a stop codon to the C-terminus of the gene. In some later constructs, the plasmid's SalI site was used for insertion in order to remove the Myc epitope from the construct. Site directed mutagenesis was performed using a QuikChange II XL kit (Stratagene, La Jolla, Calif.). All constructs and mutations were confirmed by sequencing.

Protein Production and Purification: Protein was produced in *E. coli* LMG 194 cells grown at 32° C. in Terrific Broth. Cultures were allowed to reach an $OD_{600}$ of 0.7 and were then induced by addition of L-(+)-Arabinose to a final concentration of 0.2%. 12-14 hours later, cells were harvested and the periplasm extracted by osmotic shock.

Figure 12:
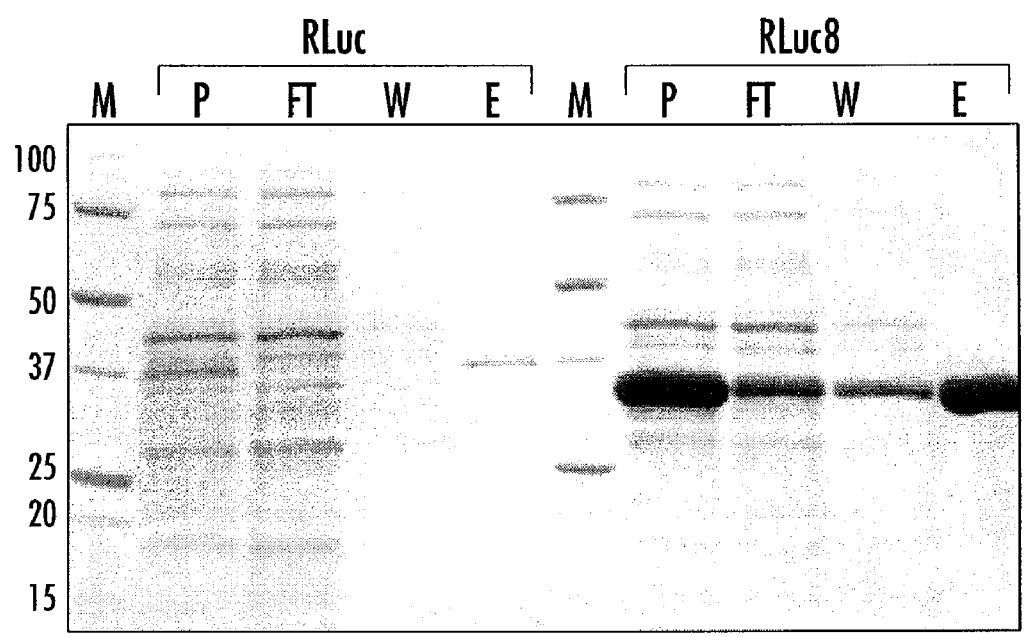
FIG. 12 illustrates the coomassie stained SDS-PAGE gel of RLuc and RLuc8 at several points during the purification process. The lanes are labeled as follows: M—Marker, P—Periplasmic fraction, FT—Flow through from nickel affinity column, W—Wash from column, and E—Elution from column. As the elution volume is 5% of the periplasmic fraction, the periplasmic fraction, flow through, and wash were concentrated twenty fold using 3 kDa cut-off centrifugal concentrators (Pall, Ann Arbor, Mich.). The expected sizes for RLuc and RLuc8 are 38.7 kDa and 36.9 kDa, respectively, with the difference in size arising from a Myc epitope added by the expression vector used for RLuc. These protein masses were confirmed by MALDI-TOF. Final recovery of purified protein was typically 5 mg/L of culture for RLuc, and 50 mg/L of culture for RLuc8.

The periplasmic fraction was brought to the same concentration as the wash buffer (WB: 300 mM NaCl, 20 mM HEPES, 20 mM imidazole, pH 8) using a 10× stock, and Phenylmethylsulphonylfluoride (PMSF) was added to 1 mM. The solution was clarified by 0.2 μm filtration and ran over a nickel affinity column (Ni-NTA Superflow, Qiagen, Valencia, Calif.). The column was washed with WB and eluted with elution buffer (EB: 300 mM NaCl, 20 mM HEPES, 250 mM imidazole, pH 8). Protein concentration measurements were made using the Bradford assay with human serum albumin (HSA: Baxter Healthcare Corporation, Glendale, Calif.) as the standard. Aliquots were taken at this point for gel electrophoresis (FIG. 12). To the remainder of the elution, HSA was added to 1% as a carrier protein. All samples were stored at 4° C.

Characterization of *Renilla* Luciferase Mutants: Luciferase activity was measured by adding 1 μl of sample (diluted as necessary in EB containing 1% HSA) to 100 μl room temperature 100 mM sodium phosphate buffer (pH 7), manually adding 1 μl of 0.5 μg/μl coelenterazine or analog, manually mixing, and reading for 10 s in a luminometer. The time between the addition of the luciferin and the start of measurement was approximately 4 s.

Serum stability measurements were done by mixing 0.5 μl dilute Luciferase with either 20 μl mouse serum or 50 μl rat serum (Equitech-Bio, Kerrville, Tex.) placing the sample in a 37° C. incubator, and removing aliquots for activity testing. To calculate serum half-lives, mono-exponential decay curves were fit to the serum stability data using a Nelder/Mead Simplex non-linear least squares minimization algorithm provided by the Octave numerical programming language. Emission spectra at ambient temperature were measured using a Triax 320 (Horiba Jobin Yvon, Edison, N.J.), which incorporates an optical grating device with a liquid $N_2$ cooled CCD detector.

Protein size and monodispersity was confirmed using a Superdex 200 analytical grade gel filtration column (GE/Amersham Biosciences, Piscataway, N.J.) followed by in-line multiangle light scattering and refractive index detectors (DAWN EOS and Optilab DSP, Wyatt Technologies, Santa Barbara, Calif.). A dn/dc value of 0.185 mL/g was assumed in all calculations, and all processing was performed using the ASTRA software package (Wyatt Technologies).

For quantum yield measurements, separate 1 µl drops of protein (about 2 pm) and substrate (0.2 pm) were placed in a tube, 100 µl of 100 mM sodium phosphate buffer (pH 7) was injected by the luminometer to mix, and the total light output was integrated (generally 5-10 min). For coelenterazine-n, the protein amount was increased 10 fold and the acquisition time lengthened to insure the reaction approached completion.

Kinetics: Kinetics were assessed by injecting 100 µl of 100 mM sodium phosphate buffer (pH 7) containing coelenterazine onto 1 µl of protein (diluted appropriately in EB containing 1% HSA), and recording the light output for 20 min. The final coelenterazine concentrations tested were 118, 24, 4.7, 0.94, 0.19, and 0.038 µM. The final Luciferase concentrations were in the range of 1-7 pM. Coelenterazine absorbance was corrected for, although this was only significant for the highest concentration (10% attenuation). The values were converted from photons/s to molecules/s using the data from the quantum yield measurements, converted from flux units to mass units via integration, and processed using the kinetic curve fitting program Dynafit.

Mammalian Expression: In order to construct mammalian expression vectors, bacterial expression vectors containing the desired mutations were used as templates for PCR, with primers designed such that the N-terminal pelB sequence would be replaced by a methionine codon and a C-terminal stop codon would replace the Myc epitope and 6×His tag. The primers also contained appropriate NheI and HindIII restriction sites to allow insertion of the product into the pcDNA 3.1 plasmid (Invitrogen). The resultant plasmids were transiently transfected using SuperFect (Qiagen) into 293T or Chinese Hamster Ovarian (CHO, ATCC# CCL-61) cells growing in 24 well plates following the manufacturer's protocol. Twenty-four hours post transfection, 0.5 µg/well of coelenterazine was added, and the plates were imaged in an IVIS 50 imaging system (Xenogen, Alameda, Calif.).

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and protected by the following claims.

```
Sequences:
SEQ ID NO: 1:
  1 MASKVYDPEQ RKRMITGPQW WARCKQMNVL DSFINYYDSE KHAENAVIFLHGNAASSYLW

61 RHVVPHIEPV ARCIIPDLIG MGKSGKSGNG SYRLLDHYKY LTAWFELLNL PKKIIFVGHD

121 WGACLAFHYS YEHQDKIKAI VHAESVVDVI ESWDEWPDIE EDIALIKSEE GEKMVLENNF

181 FVETMLPSKI MRKLEPEEFA AYLEPFKEKG EVRRPTLSWP REIPLVKGGK PDVVQIVRNY

241 NAYLRASDDL PKMFIESDPG FFSNAIVEGA KKFPNTEFVK VKGLHFSQED APDEMGKYIK

301 SFVERVLKNE Q

SEQ ID NO: 2:
  1 MASKVYDPEQ RKRMITGPQW WARCKQMNVL DSFINYYDSE KHAENAVIFL HGNAASSYLW

61 RHVVPHIEPV ARCIIPDLIG MGKSGKSGNG SYRLLDHYKY LTAWFELLNL PKKIIFVGHD

121 WGAALAFHYS YEHQDKIKAI VHAESVVDVI ESWDEWPDIE EDIALIKSEE GEKMVLENNF

181 FVETVLPSKI MRKLEPEEFA AYLEPFKEKG EVRRPTLSWP REIPLVKGGK PDVVQIVRNY

241 NAYLRASDDL PKMFIESDPG FFSNAIVEGA KKFPNTEFVK VKGLHFSQED APDEMGKYIK

301 SFVERVLKNE Q

SEQ ID NO: 3:
    MASKVYDPEQ RKRMITGPQW WARCKQMNVL DSFINYYDSE KHAENAVIFL

HGNATSSYLW RHVVPHIEPV ARCIIPDLIG MGKSGKSGNG SYRLLDHYKY LTAWFELLNL

PKKIIFVGHD WGAALAFHYA YEHQDRIKAI VHMESVVDVI ESWDEWPDIE EDIALIKSEE

GEKMVLENNF FVETVLPSKI MRKLEPEEFA AYLEPFKEKG EVRRPTLSWP REIPLVKGGK

PDVVQIVRNY NAYLRASDDL PKLFIESDPG FESNAIVEGA KKFPNTEFVK VKGLHFLQED

APDEMGKYIK SFVERVLKNE Q
```

We claim:

1. A bioluminescence resonance energy transfer (BRET) system comprising: a first fusion protein including a first target protein and a bioluminescence donor molecule, wherein the bioluminescence donor molecule is a mutated *Renilla* Luciferase protein having the polypeptide sequence SEQ ID NO:3; a second fusion protein including a second target protein and a fluorescent acceptor molecule; and a bioluminescence initiating compound, wherein the bioluminescence initiating compound is a coelenterazine.

2. The BRET system of claim 1, wherein when the first fusion protein and the second fusion protein are within about 50 to 100 Angstroms of one another and in the presence of the bioluminescence initiating compound, the bioluminescence donor molecule is adapted to interact with the bioluminescence initiating compound, wherein the bioluminescence donor molecule is adapted to emit a bioluminescence energy upon interaction with the bioluminescence initiating compound, wherein the fluorescent acceptor molecule is adapted to accept the bioluminescence energy, and wherein fluorescent acceptor molecule is adapted to emit a fluorescence energy after accepting the bioluminescence.

3. The BRET system of claim 2, further comprising a cooled-CCD camera for imaging the bioluminescence energy emitted from the bioluminescence donor molecule and the fluorescence energy emitted from the fluorescent acceptor molecule.

4. A bioluminescence resonance energy transfer (BRET) system comprising: a first fusion protein including a first target protein and a bioluminescence donor molecule, wherein the bioluminescence donor molecule is a mutated *Renilla* Luciferase protein selected from: SEQ ID NO:3 or conservatively modified variants of SEQ ID NO:3 containing the specific mutations A55T, C124A, S130A, K136R, A143M, M185V, M253L and S287L, wherein the conservatively modified variant of SEQ ID NO:3 emits bioluminescence having a wavelength between about 360 to 460 nm when contacted with coelenterazine, and has an enhanced bioluminescence level relative to the wild-type *Renilla reniformis* luciferase protein when contacted with the bioluminescence compound, coelenterazine; a second fusion protein including a second target protein and a fluorescent acceptor molecule; and a bioluminescence initiating compound, wherein the bioluminescence initiating compound is a coelenterazine.

5. The BRET system of claim 4, wherein when the first fusion protein and the second fusion protein are within about 50 to 100 Angstroms of one another and in the presence of the bioluminescence initiating compound, the bioluminescence donor molecule is adapted to interact with the bioluminescence initiating compound, wherein the bioluminescence donor molecule is adapted to emit a bioluminescence energy upon interaction with the bioluminescence initiating compound, wherein the fluorescent acceptor molecule is adapted to accept the bioluminescence energy, and wherein fluorescent acceptor molecule is adapted to emit a fluorescence energy after accepting the bioluminescence.

6. The BRET system of claim 5, further comprising a cooled-CCD camera for imaging the bioluminescence energy emitted from the bioluminescence donor molecule and the fluorescence energy emitted from the fluorescent acceptor molecule.

* * * * *